US005766883A

United States Patent [19]
Ballance et al.

[11] Patent Number: 5,766,883
[45] Date of Patent: Jun. 16, 1998

[54] POLYPEPTIDES

[75] Inventors: David J. Ballance; Andrew R. Goodey, both of Nottingham, United Kingdom

[73] Assignee: Delta Biotechnology Limited, Nottingham, United Kingdom

[21] Appl. No.: 153,799

[22] Filed: Nov. 17, 1993

Related U.S. Application Data

[63] Continuation of Ser. No. 847,975, Mar. 6, 1992, abandoned, which is a continuation-in-part of Ser. No. 775,952, Oct. 29, 1991, abandoned.

[30] Foreign Application Priority Data

Apr. 29, 1989 [GB] United Kingdom ............... 8909916
Apr. 26, 1990 [WO] WIPO ....................... PCT/GB90/00650

[51] Int. Cl.$^6$ ............... C07K 14/765; C07K 19/00; C12N 5/10; C12P 21/00
[52] U.S. Cl. ............... 435/69.7; 435/254.2; 435/325; 530/363
[58] Field of Search ............... 435/69.1, 69.7, 435/252.33, 91, 240.2, 252.3, 254.11, 325; 530/350, 363

[56] References Cited

U.S. PATENT DOCUMENTS

| | | | |
|---|---|---|---|
| 4,751,180 | 6/1988 | Cousens et al. ............... 435/69.7 |
| 5,302,697 | 4/1994 | Goodey et al. ............... 530/325 |
| 5,380,712 | 1/1995 | Ballance et al. ............... 514/12 |

FOREIGN PATENT DOCUMENTS 0201239  11/1986  European Pat. Off. .

OTHER PUBLICATIONS

Hitzeman et al., Meth. Enzymol. 185:421–440, 1990.
Hedgpeth et al. Proc. Natl. Acad. Sci. vol. 77 (5) pp. 2621–25 (1980).

Primary Examiner—Eric Grimes

[57] ABSTRACT

A fusion polypeptide comprising, as at least part of the N-terminal portion thereof, an N-terminal portion of HSA or a variant thereof and, as at least part of the C-terminal portion thereof, another polypeptide except that, when the said N-terminal portion of HSA is the 1–n portion where n is 369 to 419 or a variant thereof then the said polypeptide is one of various specified entities.

The HSA-like portion may have additional N-terminal residues, such as secretion leader sequences (signal sequences). The C-terminal portion is preferably the amino terminal fragment of human urokinase-type plasminogen activator. The N-terminal and C-terminal portions may be cleavable to yield the isolated C-terminal portion, with the N-terminal portion having served to facilitate secretion from the host. Such cleavage can be achieved in yeast using a sequence cleavable by the KEX2 protease of *S. cerevisiae*.

9 Claims, 34 Drawing Sheets

FIG. 1

```
                                                              10                                           20
Asp Ala His Lys Ser Glu Val Ala His Arg Phe Lys Asp Leu Gly Glu Glu Asn Phe Lys
                                                              30                                           40
Ala Leu Val Leu Ile Ala Phe Ala Gln Tyr Leu Gln Gln Cys Pro Phe Glu Asp His Val
                                                              50                                           60
Lys Leu Val Asn Glu Val Thr Glu Phe Ala Lys Thr Cys Val Ala Asp Glu Ser Ala Glu
                                                              70                                           80
Asn Cys Asp Lys Ser Leu His Thr Leu Peh Gly Asp Lys Leu Cys Thr Val Ala Thr Leu
                                                              90                                          100
Arg Glu Thr Tyr Gly Glu Met Ala Asp Cus Cus Ala Lys Gln Glu Pro Glu Arg Asn Glu
                                                             110                                          120
Cys Phe Leu Gln His Lys Asp Asp Asn Pro Asn Leu Pro Arg Leu Val Arg Pro Glu Val
                                                             130                                          140
Asp Val Met Cys Thr Ala Phe His Asp Asn Glu Glu Thr Phe Leu Lys Lys Tyr Leu Tyr
                                                             150                                          160
Glu Ile Ala Arg Arg His Pro Tyr Phe Tyr Ala Pro Glu Leu Leu Phe Phe Ala Lys Arg
```

FIG_1A

Tyr Lys Ala Ala Phe Thr Glu Cys Cys Gln Ala Ala Asp Lys Ala Ala Cys Leu Leu Pro
170                                                                          180

Lys Leu Asp Glu Leu Arg Asp Glu Gly Lys Ala Ser Ser Ala Lys Gln Arg Leu Lys Cys
190                                                                          200

Ala Ser Leu Gln Lys Phe Gly Glu Arg Ala Phe Lys Ala Trp Ala Val Ala Arg Leu Ser
210                                                                          220

Gln Arg Phe Pro Lys Ala Glu Phe Ala Glu Val Ser Lys Leu Val Thr Asp Leu Thr Lys
230                                                                          240

Val His Thr Glu Cys Cys His Gly Asp Leu Leu Glu Cys Ala Asp Asp Arg Ala Asp Leu
250                                                                          260

Ala Lys Tyr Ile Cys Glu Asn Gln Asp Ser Ile Ser Ser Lys Leu Lys Glu Cys Cys Glu
270                                                                          280

Lys Pro Leu Leu Glu Lys Ser His Cys Ile Ala Glu Val Glu Asn Asp Glu Met Pro Ala
290                                                                          300

Asp Leu Pro Ser Leu Ala Ala Asp Phe Val Glu Ser Lys Asp Val Cys Lys Asn Try Ala
310                                                                          320

FIG. 1B

```
                                                                              340
Glu Ala Lys Asp Val Phe Leu Gly Met Phe Leu Tyr Glu Tyr Ala Arg Arg His Pro Asp
                    330
                                                                              360
Tyr Ser Val Val Leu Leu Leu Arg Leu Ala Lys Thr Tyr Glu Thr Thr Leu Glu Lys Cys
                    350
                                                                              380
Cys Ala Ala Ala Asp Pro His Glu │Cys Tyr Ala Lys Val Phe Asp Glu Phe Lys Pro Leu
                    370
                                                                              400
Val Glu Glu Pro Gln Asn Leu Ile Lys Gln Asn Cys Glu Leu Phe Glu Gln Leu Gly Glu
                    390
                                                                              420
Tyr Lys Phe Gln Asn Ala Leu Leu Val Arg Tyr Thr Lys Lys Val Pro Gln Val Ser│ Thr
                    410
                                                                              440
Pro Thr Leu Val Glu Val Ser Arg Asn Leu Gly Lys Val Gly Ser Lys Cys Cys Lys His
                    430
                                                                              460
Pro Glu Ala Lys Arg Met Pro Cys Ala Glu Asp Tyr Leu Ser Val Val Leu Asn Gln Leu
                    450
                                                                              480
Cys Val Leu His Glu Lys Thr Pro Val Ser Asp Arg Val Thr Lys Cys Cys Thr Glu Ser
                    470
```

FIG. 1C

```
                                                490         500
Leu Val Asn Arg Arg Pro Cys Pag Ser Ala Leu Glu Val Asp Glu Thr Tyr Val Pro Lys
                                                510         520
Glu Phe Asn Ala Glu Thr Phe Thr Phe His Ala Asp Ile Cys Thr Leu Ser Glu Lys Glu
                                                530         540
Arg Gln Ile Lys Lys Gln Thr Ala Leu Val Glu Leu Val Lys His Lys Pro Lys Ala Thr
                                                550         560
Lys Glu Gln Leu Lys Ala Val Met Asp Asp Phe Ala Ala Phe Val Glu Lys Cys Cys Lys
                                                570         580
Ala Asp Asp Lys Glu Thr Cys Phe Ala Glu Glu Gly Lys Lys Leu Val Ala Ala Ser Gln

Ala Ala Leu Gly Leu
```

FIG. 2

```
                 10                  20                  30                  40                  50                  60                  70                  80
        GATGCACAAGAGTGAGGTTGCTCATCGGTTTAAGGATTTGGGAGAAGAAAATTTCAAAGCCTTGGTGGTTGATTGCCTT
         D  A  H  K  S  E  V  A  H  R  F  K  D  L  G  E  E  N  F  K  A  L  V  L  I  A  F 90                 100                 110                 120                 130                 140                 150                 160
        TGCTCAGTATCTTCAGCAGTGTCCATTTGAAGATCATGTGAAGTTAGTGAATGAAGTAACTGAATTTGCAAAAACATGTG
         A  Q  Y  L  Q  Q  C  P  F  E  D  H  V  K  L  V  N  E  V  T  E  F  A  K  T  C 170                 180                 190                 200                 210                 220                 230                 240
        TGCTGATGAGTCACGTGAAAATTGTGACAAATCACTTCATACCCTTTTTGGAGACAAATTATGCACAGTTGCAACTCTT
         V  A  D  E  S  A  E  N  C  D  K  S  L  H  T  L  F  G  D  K  L  C  T  V  A  T  L 250                 260                 270                 280                 290                 300                 310                 320
        CGTGAAACCTATGGTGAAATGGCTGACTGCTGCGCCAAAGGAGAGCCTGAGAGAAATGCTTCTTGCAACACAAGA
         R  E  T  Y  G  E  M  A  D  C  C  A  K  G  E  P  E  R  N  E  C  F  L  Q  H  K  D 330                 340                 350                 360                 370                 380                 390                 400
        TGACAACCCAAACCTCCCCCGATTGGTGAGACCAGAGGTTGATGTGATGTGCACTGCTTTCATGACAATGAAGAGACAT
         D  N  P  N  L  P  R  L  V  R  P  E  V  D  D  V  M  C  T  A  F  H  D  N  E  E  T 410                 420                 430                 440                 450                 460                 470                 480
        TTTTGAAAAATACTTAAATGAAATTGCCAGAAGACATCCTTACTTTTATGCCCCGGAACTCCTTTTCTTTGCTAAAAGG
         F  L  K  K  Y  L  Y  E  I  A  R  R  H  P  Y  F  Y  A  P  E  L  L  F  F  A  K  R
```

FIG. 2A

```
      490        500        510        520        530        540        550        560
TATAAAGCTGCTTTTACAGAATGTTGCCAAGCTGCTGATAAAGCTGCCTGTTGCCAAAGCTCGATGAACTTCGGGA
 Y   K   A   A   F   T   E   C   C   G   A   K   A   C   L   L   P   K   L   D   E   L   R   D 570        580        590        600        610        620        630        640
TGAAGGGAAGGCTTCGTCTCTGCCAAACAGAGACTCAAATGTGCCAGTCTCCAAAAATTTGGAGAAAGAGCTTTCAAAGCAT
 E   G   K   A   S   S   A   K   Q   R   L   K   C   A   S   L   Q   K   F   G   E   R   A   F   K   A 650        660        670        680        690        700        710        720
GGGCAGTGGCTCGCCTGAGCCAGAGATTTCCCAAAGCTGAGTTTGCAGAAGTTCCAAGTTAGTGACAGATCTTACCAAA
 W   A   V   A   R   L   S   Q   R   F   P   K   A   E   F   A   E   V   S   K   L   V   T   D   L   T   K 730        740        750        760        770        780        790        800
GTCCACACGGAATGCTGCCATGGAGATCTGGTTGAATGTGCTGATGACAGGGCGGACCTTGCCAAGTATATCTGTGAAAA
 V   H   T   E   C   C   H   G   D   L   L   E   C   A   D   D   R   A   D   L   A   K   Y   I   C   E   N 810        820        830        840        850        860        870        880
TCAGGATTCGATCTCCAGTAAACTGAAGGAATGCTGTGAAAAACCTCTCTTGGAAAAATCCCACTGCATTGCCGAAGTGG
 Q   D   S   I   S   S   K   L   K   E   C   C   E   K   P   L   L   E   K   S   H   C   I   A   C   V 890        900        910        920        930        940        950        960
AAAATGATGAGATGCCTGCTGACTTGCCTTCATTAGCTGCTGATTTTGTTGAAAGTAAGGATGTTTGCAAAAACTATGCT
 E   N   D   E   M   P   A   D   L   P   S   L   A   A   D   F   V   E   S   K   D   V   C   K   N   Y   A
```

FIG. 2B

```
         970       980       990       1000      1010      1020      1030      1040
GAGGCAAAGGATTGCTTCCTGGGCATGTTTTTGTATGAATATGCAAGGAGGCATCCTGATTACTCTGTCGTCTGCTGCT
 E   A   K   D   V   F   L   G   M   F   L   Y   E   Y   A   R   R   H   P   D   Y   S   V   V   L   L   L 1050      1060      1070      1080      1090      1100      1110      1120
GAGACTTGCCAAAGCATAAGAGAAACCACTCTAGAGAGATCCCTCATGAATGCTATGCCAAAGTGT
 R   L   A   K   T   Y   E   T   T   L   E   K   C   C   A   A   A   D   P   H   E   C   Y   A   K   V 1130      1140      1150      1160      1170      1180      1190      2000
TCGATGAATTTAAACCCTCTGTGGAAGAGCCTCAGAATTTAATCAAACAAAACTGTGAGCTTTTTGAGCAGTTGGAGAG
 F   D   E   F   K   P   L   V   E   E   P   Q   N   L   I   K   Q   N   C   E   L   F   E   Q   L   G   E 1210      1220      1230      1240      1250      1260      1270      1280
TACAAATTCCAGAATGCGCTATTAGTTCGTTACACCAAGAAAGTACCCCAAGTGTCAACTCCAACTCTTGTAGAGGTCTC
 Y   K   F   Q   N   A   L   L   V   R   Y   T   K   K   V   P   Q   V   S   T   P   T   L   V   E   V   S 1290      1300      1310      1320      1330      1340      1350      1360
AAGAAACCTAGGAAAAGTGGGCAGCAAATGTTGTAAACATCCTGAAGCAAAAAGAATGCCTGTGCAGAAGACTATCTAT
 R   N   L   G   K   V   G   S   K   C   C   K   H   P   E   A   K   R   M   P   C   A   E   D   Y   L 1370      1380      1390      1400      1410      1420      1430      1440
CCGTGGTCCTGAACCAGTTGTGTGTTGCATGAGAAAACGCCAGTAAGTGACAGAGTCACAAAAATGCTGCACAGAGTCC
 S   V   V   L   N   Q   L   C   V   L   H   E   K   T   P   V   S   D   R   V   T   K   C   C   T   E   S
```

FIG. 2C

```
       1450       1460       1470       1480       1490       1500       1510       1520
TTGGTGAACAGGCGACCATGCTTTTCAGCTCTGGAAGTCGATGAAACATACGTTCCCAAAGAGTTTAATGCTGAAACATT
 L  V  N  R  R  P  C  F  S  A  L  E  V  D  E  T  Y  V  P  K  E  F  N  A  E  T  F 1530       1540       1550       1560       1570       1580       1590       1600
CACCTTCCATGCAGATATATGCACACTTTCTGAGAAGGAGAGACAAATCAAGAAACTGCCACTTGTTGAGCTTGTGA
 T  F  H  A  D  I  C  T  L  S  E  K  E  R  Q  I  K  K  Q  T  A  L  V  E  L  V 1610       1620       1630       1640       1650       1660       1670       1680
AACACAAGCCCAAGGCAACAAAGAGCAACTGAAAGCTGTTATGGATGATTTCGCAGCTTTTGTAGAGAAGTGCTGCAAG
 K  H  K  P  K  A  T  K  E  Q  L  K  A  V  M  D  D  F  A  A  F  V  E  K  C  C  K 1690       1700       1710       1720       1730       1740       1750       1760
GCTGACGATAAGGAGACCTGCTTTGCCGAGGAGGGTAAAAAACTTGTTGCTGCAAGTCAAGCTGCCTTAGGCTTATAACA
 A  D  D  K  E  T  C  F  A  E  E  G  K  K  L  V  A  A  S  Q  A  A  L  G  L 1770       1780
TCTACATTTAAAAGCATCTCAG
```

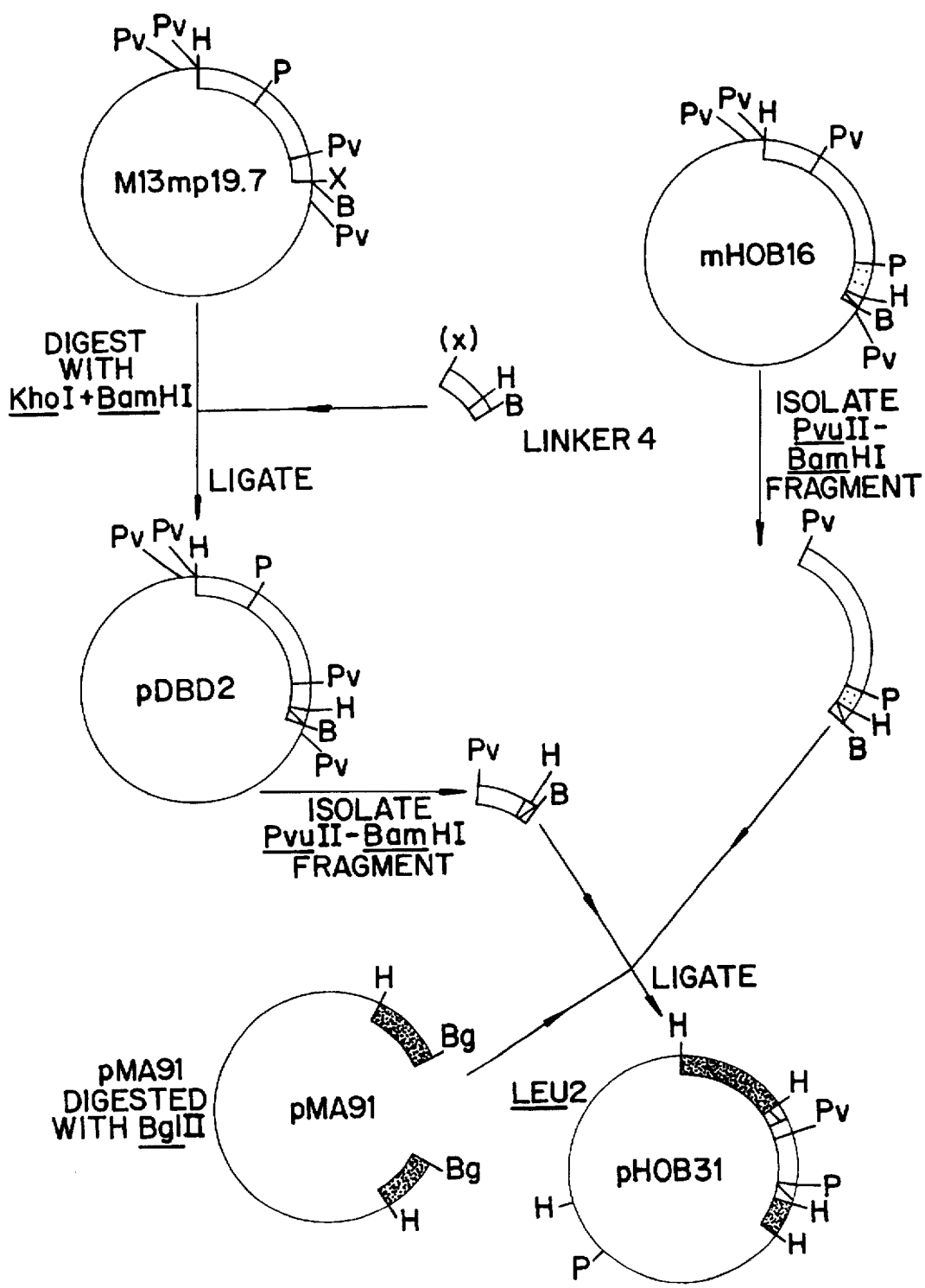
FIG_4

FIG. 5

```
                                                              10                              20
Gln Ala Gln Gln Met Val Gln Pro Gln Ser Pro Val Ala Val Ser Gln Ser Lys Pro Gly
                                                              30                              40
Cys Tyr Asp Asn Gly Lys His Tyr Gln Ile Asn Gln Gln Trp Glu Arg Thr Tyr Leu Gly
                                                              50                              60
Asn Val Leu Val Cys Thr Cys Tyr Gly Gly Ser Arg Gly Phe Asn Cys Glu Ser Lys Pro
                                                              70                              80
Glu Ala Glu Glu Thr Cys Phe Asp Lys Tyr Thr Gly Asn Thr Tyr Arg Val Gly Asp Thr
                                                              90                              100
Tyr Glu Arg Pro Lys Asp Ser Met Ile Trp Asp Cys Thr Cys Ile Gly Ala Gly Arg Gly
                                                              110                             120
Arg Ile Ser Cys Thr Ile Ala Asn Arg Cys His Glu Gly Gly Gln Ser Tyr Lys Ile Gly
                                                              130                             140
Asp Thr Trp Arg Arg Pro His Glu Thr Gly Gly Tyr Met Leu Glu Cys Val Cys Leu Gly
                                                              150                             160
Asn Gly Lys Gly Glu Trp Thr Cys Lys Pro Ile Ala Glu Lys Cys Phe Asp His Ala Ala
```

FIG. 5A

```
                                                                          180
Gly Thr Ser Tyr Val Val Gly Glu Thr Trp Glu Lys Pro Tyr Gln Gly Trp Met Met Val
                        170                                               200
Asp Cys Thr Cys Leu Gly Glu Gly Ser Gly Arg Ile Thr Cys Thr Ser Arg Asn Arg Cys
                        190                                               220
Asn Asp Gln Asp Thr Arg Thr Ser Tyr Arg Ile Gly Asp Thr Trp Ser Lys Lys Asp Ans
                        210                                               240
Arg Gly Asn Leu Leu Gln Cys Ile Cys Thr Gly Asn Gly Arg Gly Glu Trp Lys Cys Glu
                        230                                               260
Arg His Thr Ser Val Gln Thr Thr Ser Ser Gly Ser Gly Pro Phe Thr Asp Val Arg Ala
                        250                                               280
Ala Val Tyr Gln Pro Gln Pro His Pro Gln Pro Pro Pro Tyr Gly His Cys Val Thr Asp
                        270                                               300
Ser Ely Val Val Tyr Ser Val Gly Met Gln Trp Leu Lys Thr Gln Gly Asn Lys Gln Met
                        290                                               320
Leu Cys Thr Cys Leu Gly Asn Gly Val Ser Cys Gln Glu Thr Ala Val Thr Gln Thr Tyr
                        310
```

FIG. 5B

```
Gly Gly Asn Ser Asn Gly Glu Pro Cys Val Leu Pro Phe Thr Tyr Asn Gly Arg Thr Phe
                                330                                         340
Tyr Ser Cys Thr Thr Glu Gly Arg Gln Asp Gly His Leu Trp Cys Ser Thr Thr Ser Asn
                                350                                         360
Tyr Glu Gln Asp Gln Lys Tyr Ser Phe Cys Thr Asp His Thr Val Leu Val Gln Thr Gln
                                370                                         380
Gly Gly Asn Ser Asn Ely Ala Leu Cys His Phe Pro Phe Leu Tyr Asn Asn His Asn Tyr
                                390                                         400
Thr Asp Cys Thr Ser Glu Gly Arg Arg Asp Asn Met Lys Trp Cys Gly Thr Thr Gln Asn
                                410                                         420
FNDEL 1
Tyr Asp Ala Asp Gln Lys Phe Gly Phe Cys Pro Met Ala Ala His Glu Glu Ile Cys Thr
                                430                                         440
Thr Asn Glu Gly Val Met Tyr Arg Ile Gly Asp Gln Trp Asp Lys Gln His Asp Met Gly
                                450                                         460
His Met Met Arg Cys Thr Cys Val Gly Asn Gly Arg Gly Glu Trp Thr Cys Tyr Ala Tyr
                                470                                         480
```

FIG. 5C

Ser Gln Leu Arg Asp Gln Cys Ile Val Asp Asp Ile Thr Tyr Asn Val Asn Asp Thr Phe
                    490                         500
His Lys Arg His Glu Gly His Met Leu Asn Cys Thr Cys Phe Gly Gln Gly Arg Gly
            510                         520
Arg Trp Lys Cys Asp Pro Val Asp Gln Cys Gln Asp Ser Glu Thr Gly Thr Phe Tyr Gln
                    530                         540
Ile Gly Asp Ser Trp Glu Lys Tyr Val His Gly Val Arg Tyr Gln Cys Tyr Cys Tyr Gly
                    550                         560
Arg Gly Ile Gly Glu Trp His Cys Gln Pro Leu Gln Thr Tyr Pro Ser Ser Ser Gly Pro
                    570                         580
Val Glu Val Phe Ile Thr Glu Thr Pro Ser Gln Pro Asn Ser His Pro Ile Gln Trp Asn
                    590                         600
Ala Pro Gln Pro Ser His Ile Ser Lys Tyr Ile Leu Arg Trp Arg Pro Lys Asn Ser Val
                    610                         620
Gly Arg Trp Lys Glu Ala Thr Ile Pro Gly His Leu Asn Ser Tyr Thr Ile Lys Gly Leu
                    630                         640

FIG. 5D

```
Lys Pro Gly Val Val Tyr Glu Gly Glr Leu Ile Ser Ile Gln Gln Tyr Gly His Gln Glu
                                    650                              660
Val Thr Arg Phe Asp Phe Thr Thr Ser Thr Ser Thr Pro Val Thr Ser Asn Thr Val
                    670                              680
Thr Gly Glu Thr Thr Pro Phe Ser Pro Leu Val Ala Thr Ser Glu Ser Val Thr Glu Ile
                                    690                              700
Thr Ala Ser Ser Phe Val Val Ser Trp Val Ser Ala Ser Asp Thr Val Ser Gly Phe Arg
                                    710                              720
Val Glu Tyr Glu Leu Ser Glu Glu Gly Asp Glu Pro Gln Tyr Leu Asp Leu Pro Ser Thr
                                    730                              740
Ala Thr Ser Val Asn Ile Pro Asp Leu Leu Pro Ely Arg Lys Tyr Ile Val Asn Val Tyr
                                    750                              760
Gln Ile Ser Glu Asp Gly Glu Gln Ser Leu Ile Leu Ser Thr Ser Gln Thr Thr Ala Pro
                                    770                              780
Asp Ala Pro Pro Asp Pro Thr Val Asp Gln Val Asp Asp Thr Ser Ile Val Val Arg Trp
                            790                              800
```

FIG. 5E

```
                                                                              810                                 820
Ser Arg Pro Gln Ala Pro Ile Thr Gly Tyr Arg Ile Val Tyr Ser Pro Ser Val Glu Gly
                                            830                                 840
Ser Ser Thr Glu Leu Asn Leu Pro Glu Thr Ala Asn Ser Val Thr Leu Ser Asp Leu Gln
FNDEL 1                                     850                                 860
Pro Gly Val Gln Tyr Asn Ile Tyr Ala Val Glu Gln Asn Gln Glu Ser Thr Pro
                                            870                                 880
Val Val Ile Gln Gln Glu Thr Thr Gly Thr Pro Arg Ser Asp Thr Val Pro Ser Pro Arg
                                            890                                 900
Asp Leu Gln Phe Val Glu Val Thr Asp Val Lys Val Thr Ile Met Trp Thr Pro Pro Glu
                                            910                                 920
Ser Ala Val Thr Gly Tyr Arg Val Asp Val Ile Pro Val Asn Leu Pro Gly Glu His Gly
                                            930                                 940
Gln Arg Leu Pro Ile Ser Arg Asn Thr Phe Ala Glu Val Thr Gly Leu Ser Pro Gly Val
                                            950                                 960
Thr Tyr Tyr Phe Lys Val Phe Ala Val Ser His Gly Arg Glu Ser Lys Pro Leu Thr Ala
```

FIG. 5F

```
                                                                              980
Gln Gln Thr Thr Lys Leu Asp Ala Pro Thr Asn Leu Gln Phe Val Asn Glu Thr Asp Ser
                                                                             1000
Thr Val Leu Val Arg Trp Thr Pro Pro Arg Ala Gln Ile Thr Gly Tyr Arg Leu Thr Val
                                                                             1020
Gly Leu Thr Arg Arg Gly Gln Pro Arg Gln Tyr Asn Val Gly Pro Ser Val Ser Lys Tyr
                                                                             1040
Pro Leu Arg Asn Leu Gln Pro Ala Ser Glu Tyr Thr Val Ser Leu Val Ala Ile Lys Gly
                                                                             1060
Asn Gln Glu Ser Pro Lys Ala Thr Gly Val Phe Thr Thr Leu Gln Pro Gly Ser Ser Ile
                                                                             1080
Pro Pro Tyr Asn Thr Glu Val Thr Glu Thr Thr Ile Val Ile Thr Trp Thr Pro Ala Pro
                                                                             1100
Arg Ile Gly Phe Lys Leu Gly Val Arg Pro Ser Gln Gly Gly Glu Ala Pro Arg Glu Val
                                                                             1120
Thr Ser Asp Ser Gly Ser Ile Val Val Ser Gly Leu Thr Pro Gly Val Glu Tyr Val Tyr
```

FIG. 5G

Thr Ile Gln Val Leu Arg Asp Gly Gln Glu Arg Asp Ala Pro Ile Val Asn Lys Val Val
1130                                                                         1140
Thr Pro Leu Ser Pro Pro Thr Asn Leu His Leu Glu Ala Asn Pro Asp Thr Gly Val Leu
1150                                                                         1160
Thr Val Ser Trp Glu Arg Ser Thr Thr Pro Asp Ile Thr Gly Tyr Arg Ile Thr Thr Thr
1170                                                                         1180
Pro Thr Asn Gly Gln Gln Gly Asn Ser Leu Glu Glu Val Val His Ala Asp Gln Ser Ser
1190                                                                         1200
Cys Thr Phe Asp Asn Leu Ser Pro Gly Leu Glu Tyr Asn Val Ser Val Tyr Thr Val Lys
1210                                                                         1220
Asp Asp Lys Glu Ser Val Pro Ile Ser Asp Thr Ile Ile Pro Ala Val Pro Pro Pro Thr
1230                                                                         1240
Asp Leu Arg Phe Thr Asn Ile Gly Pro Asp Thr Met Arg Val Thr Trp Ala Pro Pro Pro
1250                                                                         1260
FNDEL 1
Ser Ile Asp Leu Thr Asn Phe Leu Val Arg Tyr Ser Pro Val Lys Asn Glu Glu Asp Val
1270                                                                         1280

FIG. 5H

Ala Glu Leu Ser Ile Ser Pro Ser Asp Asn Ala Val Val Leu Thr Asn Leu Leu Pro Gly
1290                                                                    1300
Thr Glu Tyr Val Val Ser Val Ser Ser Val Tyr Glu Gln His Glu Ser Thr Pro Leu Arg
     1310                                                   1320
Gly Arg Gln Lys Thr Gly Leu Asp Ser Pro Thr Gly Ile Asp Phe Ser Asp Ile Thr Ala
          1330                                             1340
Asn Ser Phe Thr Val His Trp Ile Ala Pro Arg Ala Thr Ile Thr Gly Tyr Arg Ile Arg
               1350                                            1360
His His Pro Glu His Phe Ser Gly Arg Pro Arg Glu Asp Arg Val Pro His Ser Arg Asn
                    1370                                              1380
Ser Ile Thr Leu Thr Asn Leu Thr Pro Gly Thr Glu Tyr Val Val Ser Ile Val Ala Leu
                         1390                                            1400
Asn Gly Arg Glu Glu Ser Pro Leu Leu Ile Gly Gln Gln Ser Thr Val Ser Asp Val Pro
                              1410                                            1420
Arg Asp Leu Glu Val Val Ala Ala Thr Pro Thr Ser Leu Leu Ile Ser Trp Asp Ala Pro
                                   1430                                           1440

FIG. 5I

```
                                                                                        1460
Ala Val Thr Val Arg Tyr Tyr Arg Ile Thr Tyr Gly Glu Thr Gly Gly Asn Ser Pro Val
                            1450
                                                                                        1480
Gln Glu Phe Thr Val Pro Gly Ser Lys Ser Thr Ala Thr Ile Ser Gly Leu Lys Pro Gly
                            1470
                                                                                        1500
Val Asp Tyr Thr Ile Thr Val Tyr Ala Val Thr Gly Arg Gly Asp Ser Pro Ala Ser Ser
                            1490
                                                                                        1520
Lys Pro Ile Ser Ile Asn Tyr Arg Thr Glu Ile Asp Lys Pro Ser Gln Met Gln Val Thr
                            1510
                                                                                        1540
Asp Val Gln Asp Asn Ser Ile Ser Val Lys Trp Leu Pro Ser Ser Ser Pro Val Thr Gly
                            1530
                                                                                        1560
Tyr Arg Val Thr Thr Thr Pro Lys Asn Gly Pro Gly Pro Thr Lys Thr Lys Thr Ala Gly
                            1550
                                                                                        1580
Pro Asp Gln Thr Glu Met Thr Ile Glu Gly Leu Gln Pro Thr Val Glu Tyr Val Val Ser
                            1570
                                                                                        1600
Val Tyr Ala Gln Asn Pro Ser Gly Glu Ser Gln Pro Leu Val Gln Thr Ala Val Thr Thr
                            1590
```

FIG. 5J

```
                                                      1610                                              1620
Ile Pro Ala Pro Thr Asp Leu Lys Phe Thr Gln Val Thr Pro Thr Ser Leu Ser Ala Gln
                          1630                                              1640
Trp Thr Pro Pro Asn Val Gln Leu Thr Gly Tyr Arg Val Arg Val Thr Pro Lys Glu Lys
                          1650                                              1660
Thr Gly Pro Met Lys Glu Ile Asn Leu Ala Pro Asp Ser Ser Ser Val Val Ser Gly
                          1670                                              1680
Leu Met Val Ala Thr Lys Tyr Glu Val Ser Val Tyr Ala Leu Lys Asp Thr Leu Thr Ser

FNDEL 1                   1690                                              1700
Arg Pro Ala Gln Gly Val Val Thr Thr Leu Glu Asn Val Ser Pro Arg Arg Ala Arg
                          1710                                              1720
Val Thr Asp Ala Thr Glu Thr Thr Ile Thr Ile Ser Trp Arg Thr Lys Thr Glu Thr Ile
                          1730                                              1740
Thr Gly Phe Gln Val Asp Ala Val Pro Ala Asn Gly Gln Thr Pro Ile Gln Arg Thr Ile
                          1750                                              1760
Lys Pro Asp Val Arg Ser Tyr Thr Ile Thr Gly Leu Gln Pro Gly Thr Asp Tyr Lys Ile
```

FIG. 5K

```
Tyr Leu Tyr Thr Lau Asn Asp Asn Ala Arg Ser Ser Pro Val Val Ile Asp Ala Ser Thr
                            1770                                    1780

Ala Ile Asp Ala Pro Ser Asn Lau Arg Phe Lau Ala Thr Thr Pro Asn Ser Leu Leu Val
                            1790                                    1800

Ser Trp Gln Pro Pro Arg Ala Arg Ile Thr Gly Tyr Ile Ile Lys Tyr Glu Lys Pro Gly
                            1810                                    1820

Ser Pro Pro Arg Glu Val Val Pro Arg Pro Arg Pro Gly Val Thr Glu Ala Thr Ile Thr
                            1830                                    1840

Gly Leu Glu Pro Gly Thr Glu Tyr Thr Ile Tyr Val Ile Ala Leu Lys Asn Asn Gln Lys
                            1850                                    1860

Ser Glu Pro Leu Ile Gly Arg Lys Lys Thr Aso Glu Leu Pro Gln Leu Val Thr Leu Pro
                            1870                                    1880

His Pro Asn Leu His Gly Pro Glu Ile Leu Asp Val Pro Ser Thr Val Gln Lys Thr Pro
                            1890                                    1900

Phe Val Thr His Pro Gly Tyr Asp Thr Gly Asn Gly Ile Gln Leu Pro Gly Thr Ser Gly
                            1910                                    1920
```

FIG. 5L

```
     1930                1940
Gln Gln Pro Ser Val Gly Gln Met Ile Phe Glu Glu His Gly Phe Arg Arg Thr Thr
     1950                1960
Pro Pro Thr Thr Ala Thr Pro Ile Arg His Arg Pro Arg Pro Tyr Pro Pro Asn Val Ala
     1970                1980
Leu Ser Gln Thr Thr Ile Ser Trp Ala Pro Phe Gln Aso Thr Ser Glu Tyr Ile Ile Ser
     1990                2000
Cys His Pro Val Gly Thr Asp Glu Glu Pro Leu Gln Phe Arg Val Pro Gly Thr Ser Thr
     2010                2020
Ser Ala Thr Leu Thr Gly Leu Thr Arg Gly Ala Thr Tyr Asn Ile Ile Val Glu Ala Leu
     2030                2040
Lys Asp Gln Arg His Lys Val Arg Elu Glu Val Val Thr Val Gly Asn Ser Val Asn
     2050                2060
Glu Gly Leu Asn Gln Pro Thr Asp Asp Ser Cys Phe Asp Pro Tyr Thr Val Ser His Tyr
     2070                2080
Ala Val Gly Asp Glu Trp Glu Arg Met Ser Glu Ser Gly Phe Lys Leu Leu Cys Gln Cys
```

FIG. 5M

```
                                                              2090                                    2100
Leu Ser Phe Gly Ser Gly His Phe Arg Cys Asp Ser Ser Arg Trp Cys His Asp Asn Gly
FNDEL 1                                                       2110                                    2120
Val Asn Tyr Lys Ile Gly Glu Lys Trp Asp Arg Gln Gly Glu Asn Gly Gln Met Met Ser
                                                              2130                                    2140
Cys Thr Cys Leu Gly Asn Gly Lys Gly Glu Phe Lys Cys Asp Pro His Glu Ala Thr Cys
                                                              2150                                    2160
Tyr Asp Asp Gly Lys Thr Tyr His Val Gly Glu Gln Trp Gln Lys Glu Tyr Leu Gly Ala
                                                              2170                                    2180
Ile Cys Ser Cys Thr Cys Phe Gly Gly Gln Arg Gly Trp Arg Cys Asp Asn Cys Arg Arg
                                                              2190                                    2200
Pro Gly Gly Glu Pro Ser Pro Glu Gly Thr Thr Gly Gln Ser Tyr Asn Gln Tyr Ser Gln
                                                              2210                                    2220
Arg Tyr His Gln Arg Thr Asn Thr Asn Val Asn Cys Pro Ile Glu Cys Phe Met Pro Leu
                                                              2230
Asp Val Gln Ala Asp Arg Glu Asp Ser Arg Glu
```

FIG. 6

```
GAAGAGCCTCAGAATTAATCACTGAGACTCCGAGTCAGCCCAACTCCCACCCCATCCAGTGG
CTTCTCGGAGTCTTAAATTAGTGACTCTGAGGCTCAGTCGGGGTGAGGGTGGGTAGGTCACC
```
e e p q n l i t e | t p s q p n s h p p i q w
          1              8                    2

```
AATGCACCACCAGCCATCTCACATTTCCAAGTACATTCTCAGGTGGAGACCTAAAAATTCTGTA
TTACGTGGTGGTCGTAGAGTGTAAAGGTTCATGTAAGAGTCCACCTCTGGATTTTTAAGACAT
```
n a p q p | s h i s k y i l r w r p k n s v
        7                        3

```
GGCCGTTGGAAGGAAGCTACCATACCAGGCCACTTAAACTCCTACACCATCAAAGGCCCTG
CCGGCAACCTTCCTTCGATGGTATGGTCCGGTGAATTTGAGGATGGTAGTTTCCGGACTTAA
```
g | r w k e a t i p g h l n s | y t i k g l
  6                        4              5

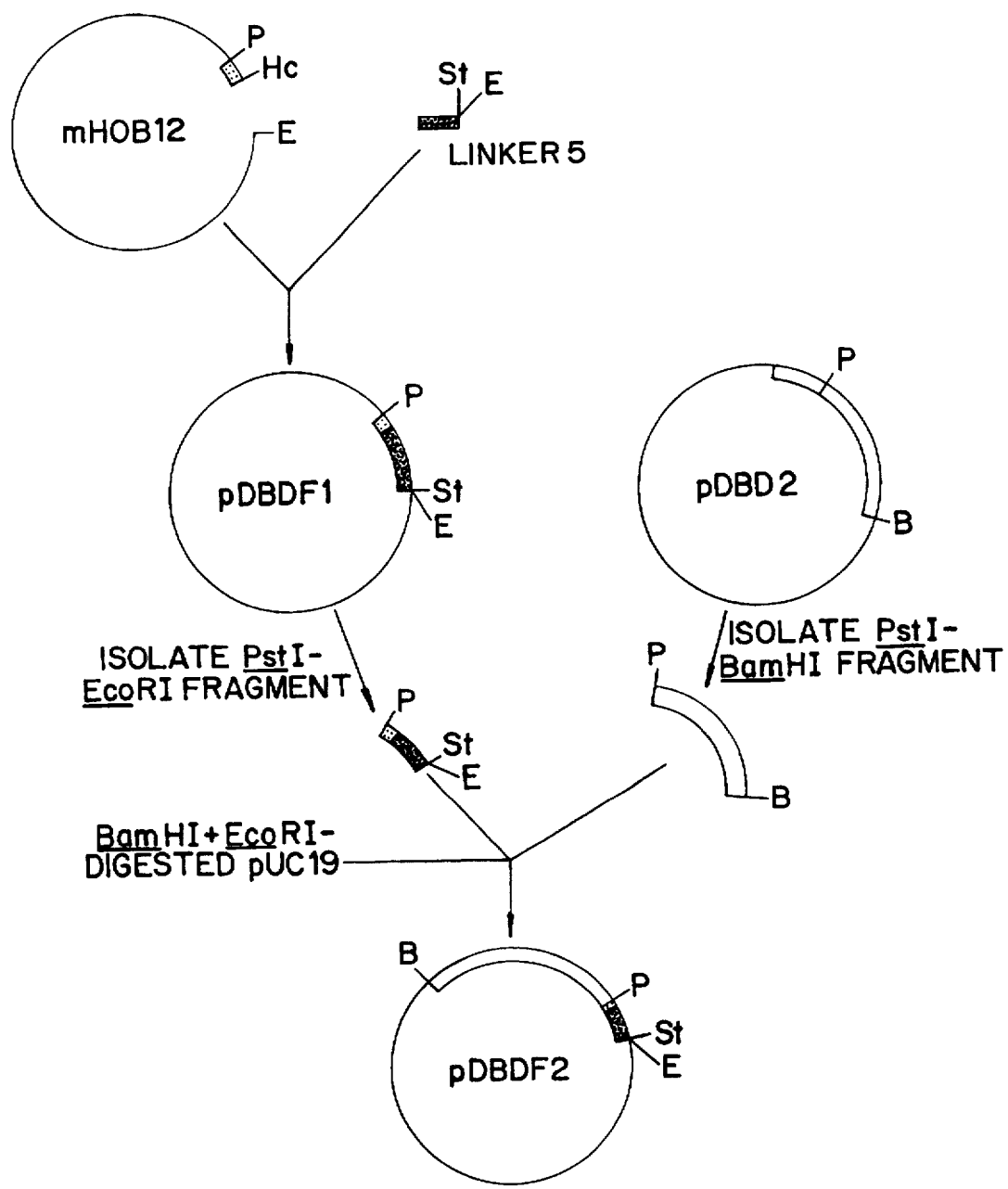
FIG_7

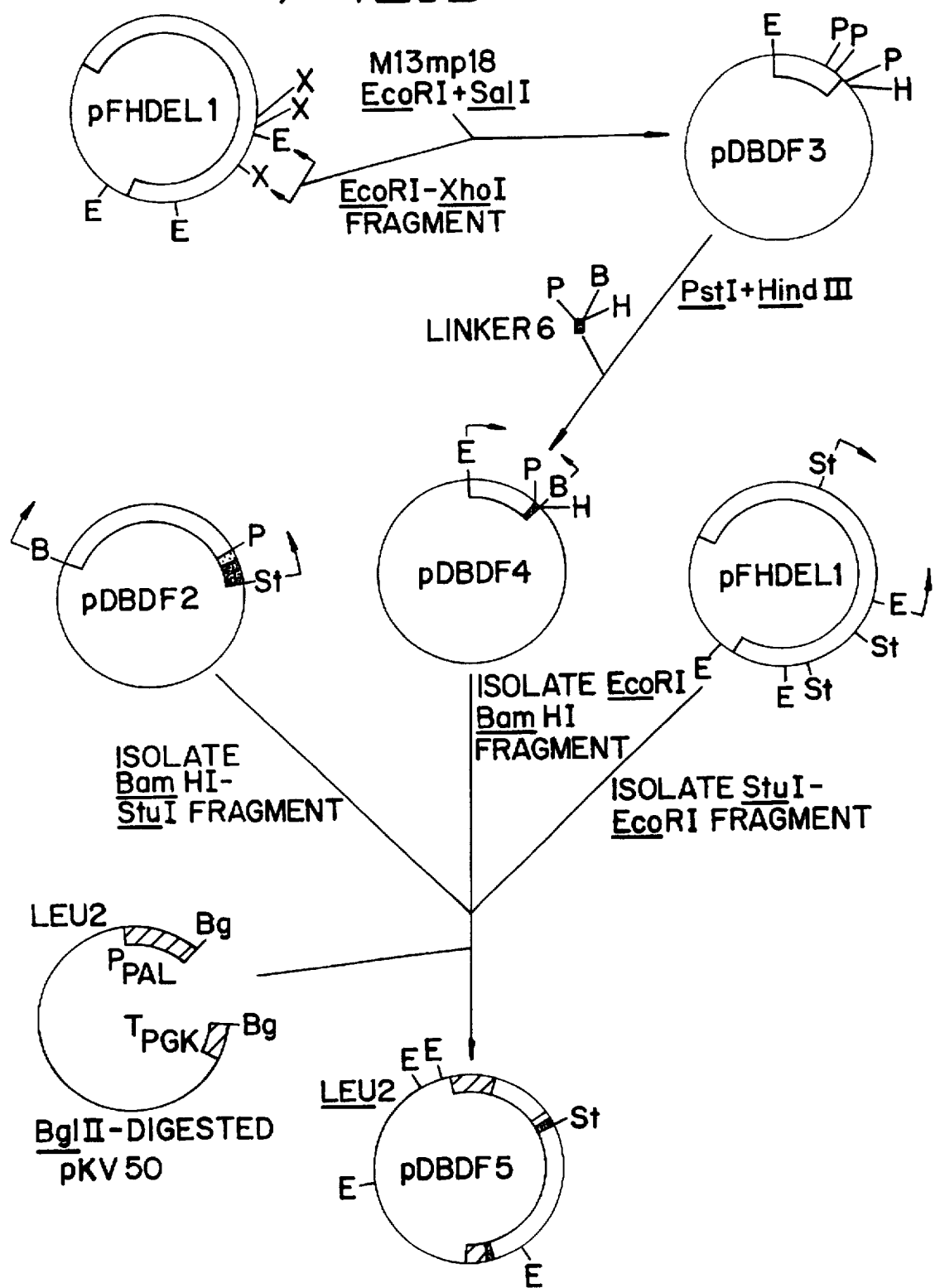
FIG_8

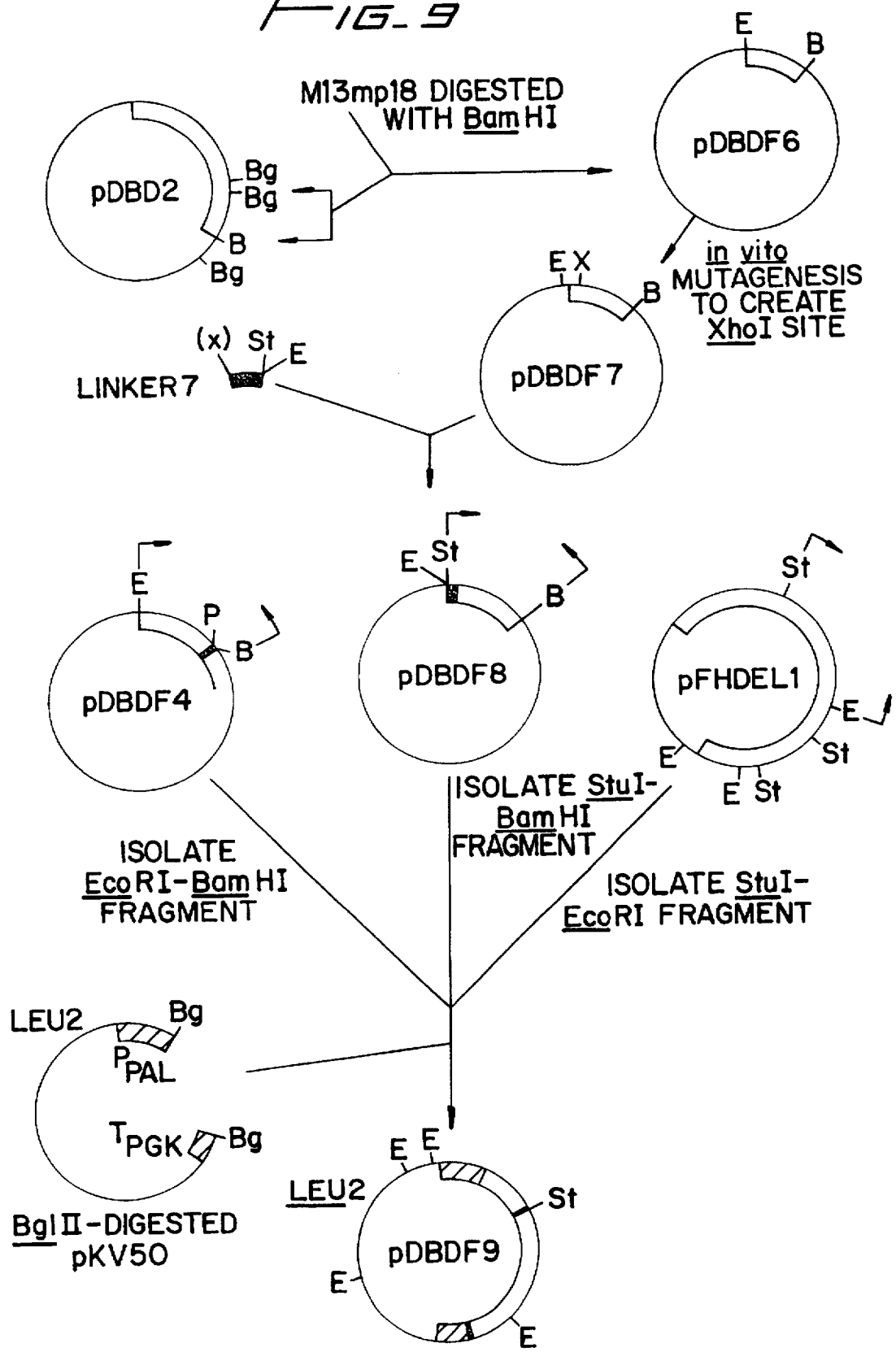

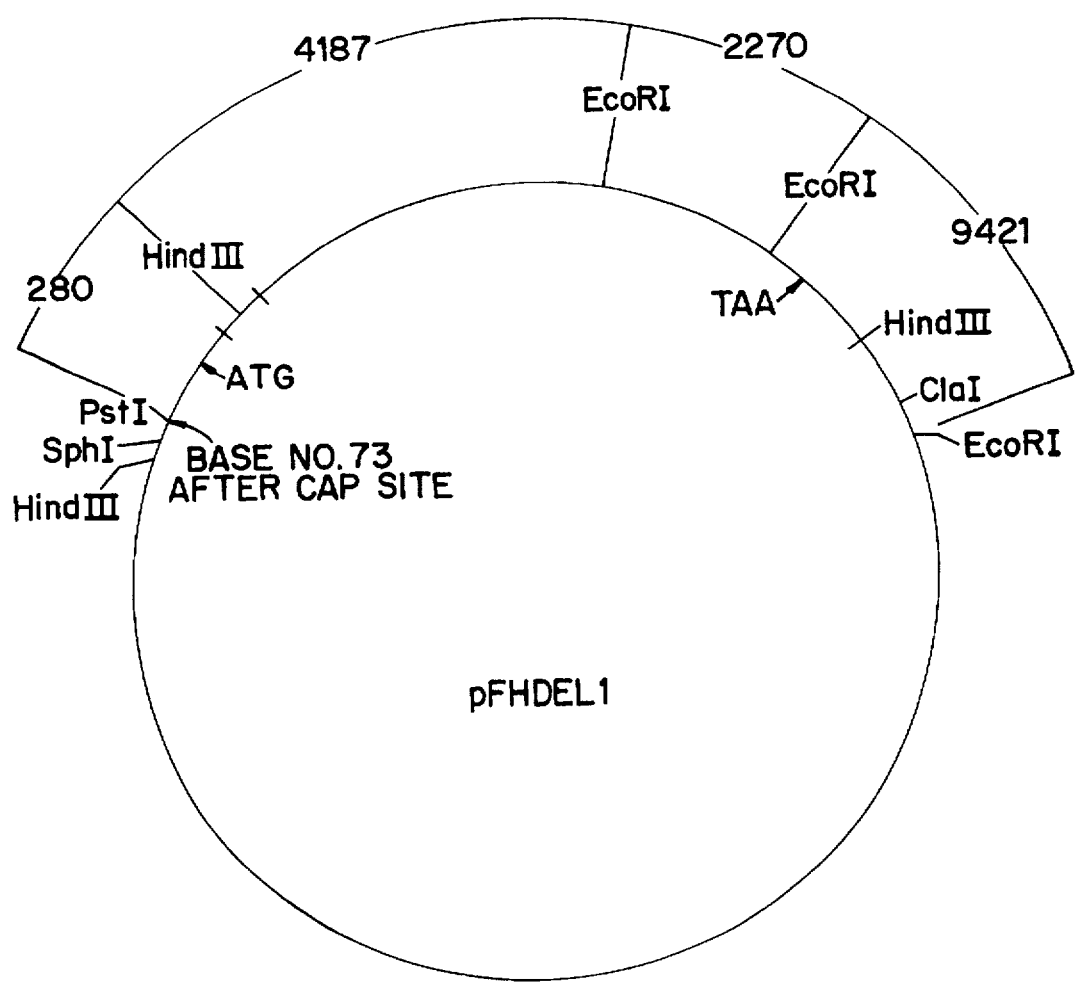
FIG_11

FIG. 12

```
    S   N   E   L   H   Q   V   P   S   N   C   D   C   L   N   G   T   C
   AGC AAT GAA CTT CAT CAA GTT CCA TCG AAC TGA GAC TGT CTA AAT GGA ACA TGT
        5'-GCT ACG GTA CCA TCG ATT CAC TGT CTA CTA AAT GG-3' ^50

V   S   N   K   Y   F   S   N   I   H   W   C   N   C   P   K   F   G
   GTG TCC AAC AAG TAC TTC TCC AAC ATT CAC TGG TGC AAC TGC CCA AAG TTC GGA
                                                           ^100

G   Q   H   C   E   I   D   K   S   K   T   C   Y   E   G   N   G   H   F
   GGG CAG CAC TGT GAA ATA GAT AAG TCA AAA ACC TGC TAT GAG AAT GGT CAC TTT
                                                   ^150

Y   R   G   K   A   S   T   D   T   M   G   R   P   C   L   P   W   N   S
   TAC CGA GGA AAG GCC AGC ACT GAC ACC ATG GGC CGG CCC CGC CTG CCC AAC TCT
                                               ^200

A   T   V   L   Q   Q   T   Y   H   A   H   R   S   D   A   L   G
   GCC ACT GTC CTT CAG CAA ACG TAC CAT GCC CAC AGA TCT GAT GCT CTT CAG CTG GGC
                                       ^250

L   G   K   H   N   Y   C   R   N   P   D   N   R   R   R   P   W   C   Y
   CTG GGG AAA CAT AAT TAC TGC AGG AAC CCA GAC AAC CGG AGG CGA CCC TGG TGC TAT
                           ^300

V   Q   V   G   L   K   P   L   V   Q   E   C   M   V   H   D   C   A   D
   GTG CAG GTG GGC CTA AAG CCA CTT GTC CAA GAG TGC ATG GTG CAT GAC TGC GTA GAT
        ^350
                                          3'-ACG TAC CAC GTA CTG ACG CGT CTA

G   K   K   P   S   S   P   P   E   E   L   K   F   Q   C   Q   K   T
   GGA AAA AAG CCC TCC TCT CCT CCA GAA GAA TTA AAA TTT CAG TGT CAA AAG ACT
   CCT ATT CCC TAG GCT AGC G-5'                              ^450
```

FIG_12A

```
L    R    P    R    F    K    I    I    G    G    E    F    T    T    I    E    N    Q    P
CTG  AGG  CCC  CGC  TTT  AAG  ATT  ATT  GGG  GGA  GAA  TTC  ACC  ATC  GAG  AAC  CAG  CCC
                                                           ^500

W    F    A    A    I    Y    R    R    H    G    G    S    V    T    Y    V    C    G
TGG  TTT  GCG  GCC  ATC  TAC  AGG  AGG  CAC  GGG  GGC  TCT  GTC  ACC  TAC  GTG  TGT  GGA
                                                           ^550

G    S    L    I    S    P    C    W    V    I    S    A    T    H    C    F    I    D    Y
GGC  AGC  CTC  ATC  AGC  CCT  TGC  TGG  GTG  ATC  AGC  GCC  ACA  CAC  TGC  TTC  ATT  GAT  TAC
                                              ^600

P    K    K    E    D    Y    I    V    Y    L    G    R    S    R    L    N    S    N    T
CCA  AAG  AAG  GAG  GAC  TAC  ATC  GTC  TAC  CTG  GGT  CGC  TCA  AGG  CTT  AAC  TCC  AAC  ACG
                                         ^650

Q    G    E    E    M    K    F    E    E    V    E    N    L    I    L    H    K    D    Y    S    A
CAA  GGG  GAG  GAG  ATG  AAG  TTT  GAG  GTG  GAA  AAC  CTC  ATC  CTA  CAC  AAG  GAC  TAC  AGC  GCT
                                    ^700

D    T    L    A    H    H    N    D    I    A    L    L    K    I    R    S    K    E    G
GAC  ACG  CTT  GCT  CAC  CAC  AAC  GAC  ATT  GCC  TTG  CTG  AAG  ATC  CGT  TCC  AAG  GAG  GGC
                    ^750

R    C    A    Q    P    S    R    T    I    Q    T    I    C    L    P    S    M    Y    N
AGG  TGT  GCG  CAG  CCA  TCC  CGG  ACT  ATA  CAG  ACC  ATC  TGC  CTG  CCC  TCG  ATG  TAT  AAC
^800                                                                            ^850
```

FIG. 12B

```
  D    P    Q    F    G    T    S    C    E    I    T    G    F    G    K    E    N    S    T
 GAT  CCC  CAG  TTT  GGC  ACA  AGC  TGT  GAG  ATC  ACT  GGC  TTT  GGA  AAA  GAG  AAT  TCT  ACC
                                                                        ^900

D    Y    L    C    Q    P    E    Q    Q    P    H    Y    G    V    E    K    M    T    V    E    K    M    T    V    H    R
 GAC  TAT  CTC  TAT  CCG  GAG  CAG  CAG  CAC  TAC  CCG  GAG  CAG  CAG  CAC  TAC  CCG  GAG  CAG  CAG  CAC  TAC  CCG  CAC  CGG

E    C    Q    P    H    Y    G    S    E    V    T    K    M    L    C    A
 GAG  TGT  CAG  CCC  CAC  TAC  GGC  TCT  GAA  GTC  ACC  AAA  ATG  CTA  TGT  GCT
                                         ^950

A    D    P    Q    W    K    T    D    S    C    Q    G    G    P    L    V
 GCT  GAC  CCC  CAA  TGG  AAA  ACA  GAT  TCC  TGC  CAG  GGA  GGA  CCC  CTC  GTC
                                              ^1000

Q    S    L    Q    G    R    M    T    L    T    G    I    V    S    W    G    R    G    C
 TGT  TCC  CTC  CAA  GGT  CGC  ATG  ACT  TTG  ACT  GGA  ATT  GTG  AGC  TGG  GGC  CGT  GGA  TGT
                              ^1100

A    L    K    D    K    P    G    V    Y    T    R    V    S    H    F    L    P    W    I
 GCC  CTG  AAG  GAC  AAG  CCA  GGC  GTC  TAC  ACG  AGA  GTC  TCA  CAC  TTC  TTA  CCC  TGG  ATC
                    ^1150

R    S    H    T    K    E    E    N    G    L    A    L   stop
 CGC  AGT  CAC  ACC  AAG  GAA  GAG  AAT  GGC  CTG  GCC  CTC  TGA
 ^1200
```

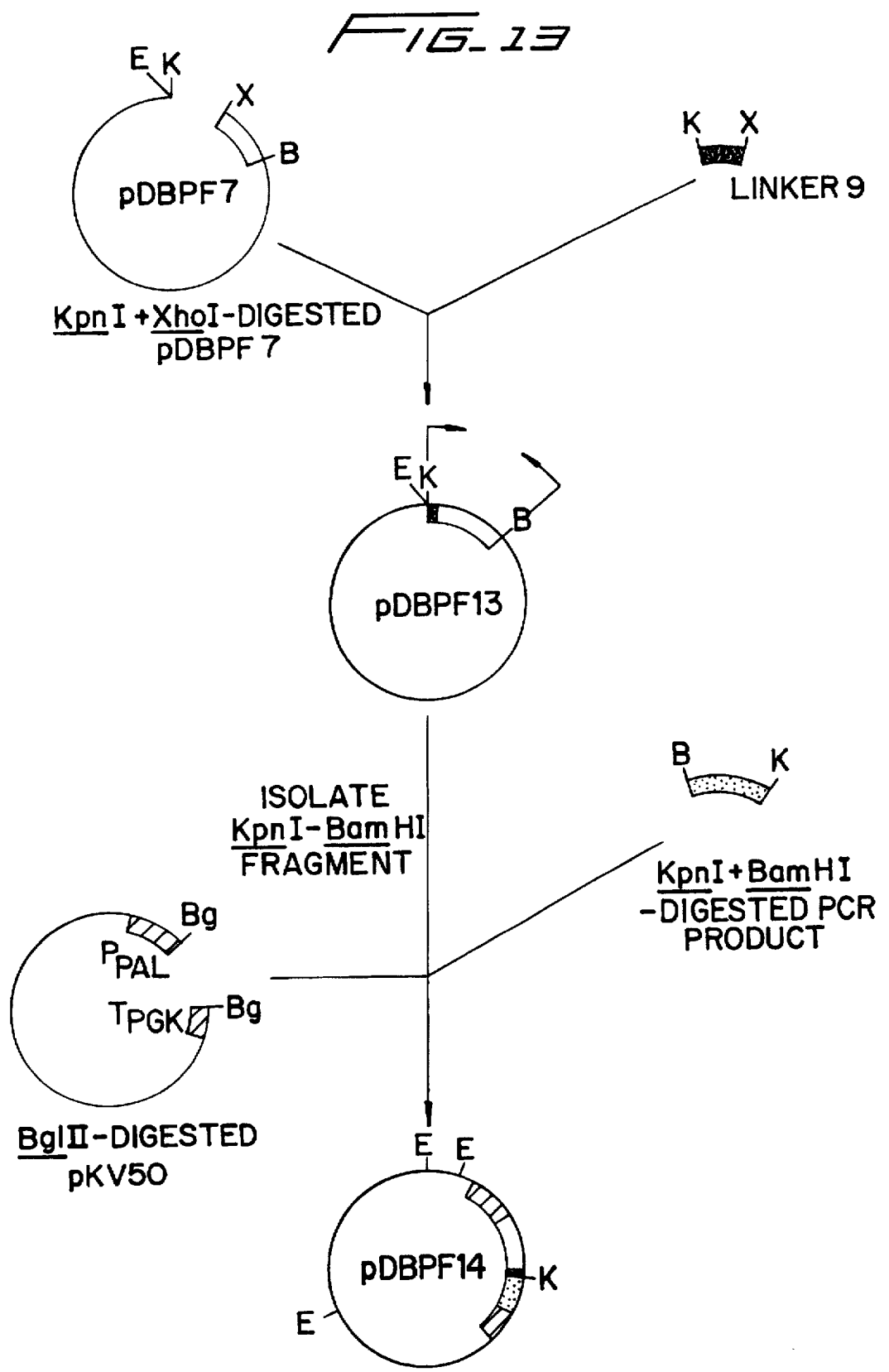
FIG_13

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 51 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( i v ) ANTI-SENSE: NO ( i x ) FEATURE:
      ( A ) NAME/KEY: misc_feature
      ( B ) LOCATION: 49..51
      ( D ) OTHER INFORMATION: /function="mutated valine codon changed from GTG to GTC"

( i x ) FEATURE:

( A ) NAME/KEY: misc_feature
                    ( B ) LOCATION: 1..51
                    ( D ) OTHER INFORMATION: /function="LINKER 1"

( x i ) SEQUENCE DESCRIPTION: SEQ ID NO:1:

GATCCTCATG AATGCTATGC CAAAGTGTTC GATGAATTTA AACCTCTTGT C         51

( 2 ) INFORMATION FOR SEQ ID NO:2:

( i ) SEQUENCE CHARACTERISTICS:
                    ( A ) LENGTH: 26 base pairs
                    ( B ) TYPE: nucleic acid
                    ( C ) STRANDEDNESS: double
                    ( D ) TOPOLOGY: linear ( i i ) MOLECULE TYPE: cDNA ( i i i ) HYPOTHETICAL: NO ( i v ) ANTI-SENSE: NO ( i x ) FEATURE:
                    ( A ) NAME/KEY: misc_feature
                    ( B ) LOCATION: 1..26
                    ( D ) OTHER INFORMATION: /function="LINKER 2"

( x i ) SEQUENCE DESCRIPTION: SEQ ID NO:2:

TCTTTTATCC AAGCTTGGAT AAAAGA                                    26

( 2 ) INFORMATION FOR SEQ ID NO:3:

( i ) SEQUENCE CHARACTERISTICS:
                    ( A ) LENGTH: 32 base pairs
                    ( B ) TYPE: nucleic acid
                    ( C ) STRANDEDNESS: double
                    ( D ) TOPOLOGY: linear ( i i ) MOLECULE TYPE: cDNA ( i x ) FEATURE:
                    ( A ) NAME/KEY: misc_feature
                    ( B ) LOCATION: 25..27
                    ( D ) OTHER INFORMATION: /function="stop codon"

( i x ) FEATURE:
                    ( A ) NAME/KEY: misc_feature
                    ( B ) LOCATION: 26..31
                    ( D ) OTHER INFORMATION: /function="HindIII site"

( i x ) FEATURE:
                    ( A ) NAME/KEY: misc_feature
                    ( B ) LOCATION: 1..32
                    ( D ) OTHER INFORMATION: /function="LINKER 3"

( x i ) SEQUENCE DESCRIPTION: SEQ ID NO:3:

GAAGAGCCTC AGAATTTAAT CAAATAAGCT TG                             32

( 2 ) INFORMATION FOR SEQ ID NO:4:

( i ) SEQUENCE CHARACTERISTICS:
                    ( A ) LENGTH: 73 base pairs
                    ( B ) TYPE: nucleic acid
                    ( C ) STRANDEDNESS: double
                    ( D ) TOPOLOGY: linear ( i i ) MOLECULE TYPE: cDNA ( i i i ) HYPOTHETICAL: NO ( i v ) ANTI-SENSE: NO ( i x ) FEATURE:
                    ( A ) NAME/KEY: misc_feature
                    ( B ) LOCATION: 17..22

(D) OTHER INFORMATION: /function="HindIII site"

(ix) FEATURE:
    (A) NAME/KEY: misc_feature
    (B) LOCATION: 1..73
    (D) OTHER INFORMATION: /function="LINKER 4"

(xi) SEQUENCE DESCRIPTION: SEQ ID NO:4:

```
GATCCATGAA GTGGGTAAGC TTTATTTCCC TTCTTTTTCT CTTTAGCTCG GCTTATTCCA    60
GGGGTGTGTT TCG                                                       73
```

(2) INFORMATION FOR SEQ ID NO:5:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..40
        (D) OTHER INFORMATION: /function="oligonucleotide 1"

(ix) FEATURE:
        (A) NAME/KEY: misc_feature
        (B) LOCATION: 41..89
        (D) OTHER INFORMATION: /function="oligonucleotide 2"

(ix) FEATURE:
        (A) NAME/KEY: misc_feature
        (B) LOCATION: 90..138
        (D) OTHER INFORMATION: /function="oligonucleotide 3"

(ix) FEATURE:
        (A) NAME/KEY: misc_feature
        (B) LOCATION: 139..186
        (D) OTHER INFORMATION: /function="oligonucleotide 4"

(ix) FEATURE:
        (A) NAME/KEY: misc_feature
        (B) LOCATION: 1..186
        (D) OTHER INFORMATION: /function="LINKER 5"

(xi) SEQUENCE DESCRIPTION: SEQ ID NO:5:

```
GAAGAGCCTC AGAATTTAAT CACTGAGACT CCGAGTCAGC CCAACTCCCA CCCCATCCAG    60
TGGAATGCAC CACAGCCATC TCACATTTCC AAGTACATTC TCAGGTGGAG ACCTAAAAAT   120
TCTGTAGGCC GTTGGAAGGA AGCTACCATA CCAGGCCACT TAAACTCCTA CACCATCAAA   180
GGCCTG                                                              186
```

(2) INFORMATION FOR SEQ ID NO:6:

(i) SEQUENCE CHARACTERISTICS:
        (A) LENGTH: 62 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature ( B ) LOCATION: 55..57
                    ( D ) OTHER INFORMATION: /function="stop codon"

( i x ) FEATURE:
                    ( A ) NAME/KEY: misc_feature
                    ( B ) LOCATION: 56..61
                    ( D ) OTHER INFORMATION: /function="HindIII site"

( i x ) FEATURE:
                    ( A ) NAME/KEY: misc_feature
                    ( B ) LOCATION: 1..62
                    ( D ) OTHER INFORMATION: /function="LINKER 6"

( x i ) SEQUENCE DESCRIPTION: SEQ ID NO:6:

GGTCCAGATC AAACAGAAAT GACTATTGAA GGCTTGCAGC CCACAGTGGA GTATTAAGCT           60

TG                                                                        62

( 2 ) INFORMATION FOR SEQ ID NO:7:

( i ) SEQUENCE CHARACTERISTICS:
                    ( A ) LENGTH: 63 base pairs
                    ( B ) TYPE: nucleic acid
                    ( C ) STRANDEDNESS: double
                    ( D ) TOPOLOGY: linear ( i i ) MOLECULE TYPE: cDNA ( i i i ) HYPOTHETICAL: NO ( i v ) ANTI-SENSE: NO ( i x ) FEATURE:
                    ( A ) NAME/KEY: misc_feature
                    ( B ) LOCATION: 1..63
                    ( D ) OTHER INFORMATION: /function="LINKER 7"

( x i ) SEQUENCE DESCRIPTION: SEQ ID NO:7:

TCGATGAACT TCGGGATGAA GGGAAGGCTT CGTCTGCCAA AATCACTGAG ACTCCGAGTC           60

AGC                                                                       63

( 2 ) INFORMATION FOR SEQ ID NO:8:

( i ) SEQUENCE CHARACTERISTICS:
                    ( A ) LENGTH: 52 base pairs
                    ( B ) TYPE: nucleic acid
                    ( C ) STRANDEDNESS: double
                    ( D ) TOPOLOGY: linear ( i i ) MOLECULE TYPE: cDNA ( i i i ) HYPOTHETICAL: NO ( i v ) ANTI-SENSE: NO ( i x ) FEATURE:
                    ( A ) NAME/KEY: misc_feature
                    ( B ) LOCATION: 19..30
                    ( D ) OTHER INFORMATION: /function="cleavage recognition
                        site for Factor X"

( i x ) FEATURE:
                    ( A ) NAME/KEY: misc_feature
                    ( B ) LOCATION: 1..52
                    ( D ) OTHER INFORMATION: /function="LINKER 8"

( x i ) SEQUENCE DESCRIPTION: SEQ ID NO:8:

GAAGAGCCTC AGAATTTAAT TGAAGGTAGA ATCACTGAGA CTCCGAGTCA GC                   52

( 2 ) INFORMATION FOR SEQ ID NO:9:

( i ) SEQUENCE CHARACTERISTICS:
                    ( A ) LENGTH: 75 base pairs (B) TYPE: nucleic acid
(C) STRANDEDNESS: double
(D) TOPOLOGY: linear (i i) MOLECULE TYPE: DNA (genomic)

(i i i) HYPOTHETICAL: NO (i v) ANTI-SENSE: NO (i x) FEATURE:
 (A) NAME/KEY: CDS
 (B) LOCATION: 3..38
 (D) OTHER INFORMATION: /product="encodes amino acids 183-194 of HSA"

(i x) FEATURE:
 (A) NAME/KEY: misc_feature
 (B) LOCATION: 39..53
 (D) OTHER INFORMATION: /function="KEX2 spacer"

(i x) FEATURE:
 (A) NAME/KEY: CDS
 (B) LOCATION: 54..74
 (D) OTHER INFORMATION: /function="encodes amino acids 1-7 of uPA"

(i x) FEATURE:
 (A) NAME/KEY: misc_feature
 (B) LOCATION: 1..75
 (D) OTHER INFORMATION: /function="LINKER 9"

(x i) SEQUENCE DESCRIPTION: SEQ ID NO:9:

```
TC GAT GAA CTT CGG GAT GAA GGG AAG GCT TCG TCT GCC AGCTTGGATA        48
   Asp Glu Leu Arg Asp Glu Gly Lys Ala Ser Ser Ala
   1               5                   10

AAAGA AGC AAT GAA CTT CAT CAG GTA C                                  75
      Ser Asn Glu Leu His Gln Val
      1               5
```

(2) INFORMATION FOR SEQ ID NO:10:

(i) SEQUENCE CHARACTERISTICS:
  (A) LENGTH: 12 amino acids
  (B) TYPE: amino acid
  (D) TOPOLOGY: linear (i i) MOLECULE TYPE: protein (x i) SEQUENCE DESCRIPTION: SEQ ID NO:10:

```
Asp Glu Leu Arg Asp Glu Gly Lys Ala Ser Ser Ala
1               5                   10
```

(2) INFORMATION FOR SEQ ID NO:11:

(i) SEQUENCE CHARACTERISTICS:
  (A) LENGTH: 7 amino acids
  (B) TYPE: amino acid
  (D) TOPOLOGY: linear (i i) MOLECULE TYPE: protein (x i) SEQUENCE DESCRIPTION: SEQ ID NO:11:

```
Ser Asn Glu Leu His Gln Val
1               5
```

(2) INFORMATION FOR SEQ ID NO:12:

(i) SEQUENCE CHARACTERISTICS:
  (A) LENGTH: 36 base pairs
  (B) TYPE: nucleic acid
  (C) STRANDEDNESS: double ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 6..11
    ( D ) OTHER INFORMATION: /function="KpnI site"

( i x ) FEATURE:
    ( A ) NAME/KEY: misc_feature
    ( B ) LOCATION: 1..36
    ( D ) OTHER INFORMATION: /product="OLIGONUCLEOTIDE 9"

( x i ) SEQUENCE DESCRIPTION: SEQ ID NO:12:

GCTACGGTAC CATCGAACTG TGACTGTTCT AAATGG                                          3 6

( 2 ) INFORMATION FOR SEQ ID NO:13:

( i ) SEQUENCE CHARACTERISTICS:
    ( A ) LENGTH: 42 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1..42
    ( D ) OTHER INFORMATION: /product="OLIGONUCLEOTIDE 10"

( x i ) SEQUENCE DESCRIPTION: SEQ ID NO:13:

GCGATCGGAT CCTTATCCAT CTGCGCAATG GTCCACCATG CA                                 4 2

( 2 ) INFORMATION FOR SEQ ID NO:14:

( i ) SEQUENCE CHARACTERISTICS:
    ( A ) LENGTH: 585 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Homo sapiens ( i x ) FEATURE:
    ( A ) NAME/KEY: Region
    ( B ) LOCATION: 369..419
    ( D ) OTHER INFORMATION: /note= "Alternative C-termini of
        HSA(1-n)"

( i x ) FEATURE:
    ( A ) NAME/KEY: Region
    ( B ) LOCATION: 1..585
    ( D ) OTHER INFORMATION: /note= "Amino acid sequence of
        natural HSA"

( x i ) SEQUENCE DESCRIPTION: SEQ ID NO:14:

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
             20                  25                  30
```

-continued

```
Gln  Cys  Pro  Phe  Glu  Asp  His  Val  Lys  Leu  Val  Asn  Glu  Val  Thr  Glu
          35                      40                          45

Phe  Ala  Lys  Thr  Cys  Val  Ala  Asp  Glu  Ser  Ala  Glu  Asn  Cys  Asp  Lys
     50                      55                      60

Ser  Leu  His  Thr  Leu  Phe  Gly  Asp  Lys  Leu  Cys  Thr  Val  Ala  Thr  Leu
65                            70                      75                      80

Arg  Glu  Thr  Tyr  Gly  Glu  Met  Ala  Asp  Cys  Cys  Ala  Lys  Gln  Glu  Pro
                    85                      90                          95

Glu  Arg  Asn  Glu  Cys  Phe  Leu  Gln  His  Lys  Asp  Asp  Asn  Pro  Asn  Leu
               100                      105                         110

Pro  Arg  Leu  Val  Arg  Pro  Glu  Val  Asp  Val  Met  Cys  Thr  Ala  Phe  His
               115                      120                         125

Asp  Asn  Glu  Glu  Thr  Phe  Leu  Lys  Lys  Tyr  Leu  Tyr  Glu  Ile  Ala  Arg
     130                      135                         140

Arg  His  Pro  Tyr  Phe  Tyr  Ala  Pro  Glu  Leu  Leu  Phe  Phe  Ala  Lys  Arg
145                      150                         155                         160

Tyr  Lys  Ala  Ala  Phe  Thr  Glu  Cys  Cys  Gln  Ala  Ala  Asp  Lys  Ala  Ala
                    165                      170                         175

Cys  Leu  Leu  Pro  Lys  Leu  Asp  Glu  Leu  Arg  Asp  Glu  Gly  Lys  Ala  Ser
               180                      185                         190

Ser  Ala  Lys  Gln  Arg  Leu  Lys  Cys  Ala  Ser  Leu  Gln  Lys  Phe  Gly  Glu
          195                      200                         205

Arg  Ala  Phe  Lys  Ala  Trp  Ala  Val  Ala  Arg  Leu  Ser  Gln  Arg  Phe  Pro
     210                      215                         220

Lys  Ala  Glu  Phe  Ala  Glu  Val  Ser  Lys  Leu  Val  Thr  Asp  Leu  Thr  Lys
225                      230                         235                         240

Val  His  Thr  Glu  Cys  Cys  His  Gly  Asp  Leu  Leu  Glu  Cys  Ala  Asp  Asp
                    245                      250                         255

Arg  Ala  Asp  Leu  Ala  Lys  Tyr  Ile  Cys  Glu  Asn  Gln  Asp  Ser  Ile  Ser
               260                      265                         270

Ser  Lys  Leu  Lys  Glu  Cys  Cys  Glu  Lys  Pro  Leu  Leu  Glu  Lys  Ser  His
          275                      280                         285

Cys  Ile  Ala  Glu  Val  Glu  Asn  Asp  Glu  Met  Pro  Ala  Asp  Leu  Pro  Ser
290                      295                         300

Leu  Ala  Ala  Asp  Phe  Val  Glu  Ser  Lys  Asp  Val  Cys  Lys  Asn  Tyr  Ala
305                      310                         315                         320

Glu  Ala  Lys  Asp  Val  Phe  Leu  Gly  Met  Phe  Leu  Tyr  Glu  Tyr  Ala  Arg
                    325                      330                         335

Arg  His  Pro  Asp  Tyr  Ser  Val  Val  Leu  Leu  Leu  Arg  Leu  Ala  Lys  Thr
               340                      345                         350

Tyr  Glu  Thr  Thr  Leu  Glu  Lys  Cys  Cys  Ala  Ala  Ala  Asp  Pro  His  Glu
          355                      360                         365

Cys  Tyr  Ala  Lys  Val  Phe  Asp  Glu  Phe  Lys  Pro  Leu  Val  Glu  Glu  Pro
     370                      375                         380

Gln  Asn  Leu  Ile  Lys  Gln  Asn  Cys  Glu  Leu  Phe  Glu  Gln  Leu  Gly  Glu
385                      390                         395                         400

Tyr  Lys  Phe  Gln  Asn  Ala  Leu  Leu  Val  Arg  Tyr  Thr  Lys  Lys  Val  Pro
                    405                      410                         415

Gln  Val  Ser  Thr  Pro  Thr  Leu  Val  Glu  Val  Ser  Arg  Asn  Leu  Gly  Lys
               420                      425                         430

Val  Gly  Ser  Lys  Cys  Cys  Lys  His  Pro  Glu  Ala  Lys  Arg  Met  Pro  Cys
          435                      440                         445

Ala  Glu  Asp  Tyr  Leu  Ser  Val  Val  Leu  Asn  Gln  Leu  Cys  Val  Leu  His
```

|   | | | | | 450 | | | | | 455 | | | | | 460 | |
|---|---|---|---|---|---|---|---|---|---|---|---|---|---|---|---|---|

Glu Lys Thr Pro Val Ser Asp Arg Val Thr Lys Cys Cys Thr Glu Ser
465                     470                 475                 480

Leu Val Asn Arg Arg Pro Cys Phe Ser Ala Leu Glu Val Asp Glu Thr
                485             490                     495

Tyr Val Pro Lys Glu Phe Asn Ala Glu Thr Phe Thr Phe His Ala Asp
            500             505                 510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
    530             535                 540

Lys Ala Val Met Asp Asp Phe Ala Ala Phe Val Glu Lys Cys Cys Lys
545             550                 555                     560

Ala Asp Asp Lys Glu Thr Cys Phe Ala Glu Glu Gly Lys Lys Leu Val
            565         570                     575

Ala Ala Ser Gln Ala Ala Leu Gly Leu
        580             585

( 2 ) INFORMATION FOR SEQ ID NO:15:

( i ) SEQUENCE CHARACTERISTICS:
        ( A ) LENGTH: 1782 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: misc_feature
        ( B ) LOCATION: 1..1782
        ( D ) OTHER INFORMATION: /function="DNA sequence coding for
            mature HSA"

( i x ) FEATURE:
        ( A ) NAME/KEY: misc_feature
        ( B ) LOCATION: 1144..1162
        ( D ) OTHER INFORMATION: /function="sequence included in
            Linker 3"

( x i ) SEQUENCE DESCRIPTION: SEQ ID NO:15:

```
GATGCACACA AGAGTGAGGT TGCTCATCGG TTTAAAGATT TGGGAGAAGA AAATTTCAAA        60

GCCTTGGTGT TGATTGCCTT TGCTCAGTAT CTTCAGCAGT GTCCATTTGA AGATCATGTA       120

AAATTAGTGA ATGAAGTAAC TGAATTTGCA AAAACATGTG TTGCTGATGA GTCAGCTGAA       180

AATTGTGACA AATCACTTCA TACCCTTTTT GGAGACAAAT TATGCACAGT TGCAACTCTT       240

CGTGAAACCT ATGGTGAAAT GGCTGACTGC TGTGCAAAAC AAGAACCTGA GAGAAATGAA       300

TGCTTCTTGC AACACAAAGA TGACAACCCA AACCTCCCCC GATTGGTGAG ACCAGAGGTT       360

GATGTGATGT GCACTGCTTT TCATGACAAT GAAGAGACAT TTTTGAAAAA ATACTTATAT       420

GAAATTGCCA GAAGACATCC TTACTTTTAT GCCCCGGAAC TCCTTTTCTT TGCTAAAAGG       480

TATAAAGCTG CTTTTACAGA ATGTTGCCAA GCTGCTGATA AAGCTGCCTG CCTGTTGCCA       540

AAGCTCGATG AACTTCGGGA TGAAGGGAAG GCTTCGTCTG CCAAACAGAG ACTCAAGTGT       600

GCCAGTCTCC AAAAATTTGG AGAAAGAGCT TTCAAAGCAT GGGCAGTAGC TCGCCTGAGC       660
```

-continued

```
CAGAGATTTC  CCAAAGCTGA  GTTGCAGAA   GTTCCAAGT   TAGTGACAGA  TCTTACCAAA   720
GTCCACACGG  AATGCTGCCA  TGGAGATCTG  CTTGAATGTG  CTGATGACAG  GGCGGACCTT   780
GCCAAGTATA  TCTGTGAAAA  TCAAGATTCG  ATCTCCAGTA  AACTGAAGGA  ATGCTGTGAA   840
AAACCTCTGT  TGGAAAAATC  CCACTGCATT  GCCGAAGTGG  AAAATGATGA  GATGCCTGCT   900
GACTTGCCTT  CATTAGCTGC  TGATTTTGTT  GAAAGTAAGG  ATGTTTGCAA  AAACTATGCT   960
GAGGCAAAGG  ATGTCTTCCT  GGGCATGTTT  TTGTATGAAT  ATGCAAGAAG  GCATCCTGAT  1020
TACTCTGTCG  TGCTGCTGCT  GAGACTTGCC  AAGACATATG  AAACCACTCT  AGAGAAGTGC  1080
TGTGCCGCTG  CAGATCCTCA  TGAATGCTAT  GCCAAAGTGT  TCGATGAATT  TAAACCTCTT  1140
GTGGAAGAGC  CTCAGAATTT  AATCAAACAA  AATTGTGAGC  TTTTTGAGCA  GCTTGGAGAG  1200
TACAAATTCC  AGAATGCGCT  ATTAGTTCGT  TACACCAAGA  AAGTACCCCA  AGTGTCAACT  1260
CCAACTCTTG  TAGAGGTCTC  AAGAAACCTA  GGAAAAGTGG  GCAGCAAATG  TTGTAAACAT  1320
CCTGAAGCAA  AAAGAATGCC  CTGTGCAGAA  GACTATCTAT  CCGTGGTCCT  GAACCAGTTA  1380
TGTGTGTTGC  ATGAGAAAAC  GCCAGTAAGT  GACAGAGTCA  CCAAATGCTG  CACAGAATCC  1440
TTGGTGAACA  GGCGACCATG  CTTTTCAGCT  CTGGAAGTCG  ATGAAACATA  CGTTCCCAAA  1500
GAGTTTAATG  CTGAAACATT  CACCTTCCAT  GCAGATATAT  GCACACTTTC  TGAGAAGGAG  1560
AGACAAATCA  AGAAACAAAC  TGCACTTGTT  GAGCTCGTGA  ACACAAGCC   CAAGGCAACA  1620
AAAGAGCAAC  TGAAAGCTGT  TATGGATGAT  TTCGCAGCTT  TTGTAGAGAA  GTGCTGCAAG  1680
GCTGACGATA  AGGAGACCTG  CTTTGCCGAG  GAGGGTAAAA  AACTTGTTGC  TGCAAGTCAA  1740
GCTGCCTTAG  GCTTATAACA  TCTACATTTA  AAAGCATCTC  AG                     1782
```

(2) INFORMATION FOR SEQ ID NO:16:

(i) SEQUENCE CHARACTERISTICS:
   (A) LENGTH: 2231 amino acids
   (B) TYPE: amino acid
   (D) TOPOLOGY: linear (ii) MOLECULE TYPE: protein (iii) HYPOTHETICAL: NO (vi) ORIGINAL SOURCE:
   (A) ORGANISM: Homo sapiens (ix) FEATURE:
   (A) NAME/KEY: Protein
   (B) LOCATION: 1..2231
   (D) OTHER INFORMATION: /note= "Human fibronectin"

(xi) SEQUENCE DESCRIPTION: SEQ ID NO:16:

```
Gln Ala Gln Gln Met Val Gln Pro Gln Ser Pro Val Ala Val Ser Gln
 1               5                  10                  15
Ser Lys Pro Gly Cys Tyr Asp Asn Gly Lys His Tyr Gln Ile Asn Gln
            20                  25                  30
Gln Trp Glu Arg Thr Tyr Leu Gly Asn Val Leu Val Cys Thr Cys Tyr
        35                  40                  45
Gly Gly Ser Arg Gly Phe Asn Cys Glu Ser Lys Pro Glu Ala Glu Glu
    50                  55                  60
Thr Cys Phe Asp Lys Tyr Thr Gly Asn Thr Tyr Arg Val Gly Asp Thr
65                  70                  75                  80
Tyr Glu Arg Pro Lys Asp Ser Met Ile Trp Asp Cys Thr Cys Ile Gly
            85                  90                  95
Ala Gly Arg Gly Arg Ile Ser Cys Thr Ile Ala Asn Arg Cys His Glu
       100                 105                 110
```

```
Gly Gly Gln Ser Tyr Lys Ile Gly Asp Thr Trp Arg Arg Pro His Glu
            115                 120                 125
Thr Gly Gly Tyr Met Leu Glu Cys Val Cys Leu Gly Asn Gly Lys Gly
    130                 135                 140
Glu Trp Thr Cys Lys Pro Ile Ala Glu Lys Cys Phe Asp His Ala Ala
145                 150                 155                 160
Gly Thr Ser Tyr Val Val Gly Glu Thr Trp Glu Lys Pro Tyr Gln Gly
                165                 170                 175
Trp Met Met Val Asp Cys Thr Cys Leu Gly Glu Gly Ser Gly Arg Ile
            180                 185                 190
Thr Cys Thr Ser Arg Asn Arg Cys Asn Asp Gln Asp Thr Arg Thr Ser
        195                 200                 205
Tyr Arg Ile Gly Asp Thr Trp Ser Lys Lys Asp Asn Arg Gly Asn Leu
    210                 215                 220
Leu Gln Cys Ile Cys Thr Gly Asn Gly Arg Gly Glu Trp Lys Cys Glu
225                 230                 235                 240
Arg His Thr Ser Val Gln Thr Thr Ser Ser Gly Ser Gly Pro Phe Thr
                245                 250                 255
Asp Val Arg Ala Ala Val Tyr Gln Pro Gln Pro His Pro Gln Pro Pro
            260                 265                 270
Pro Tyr Gly His Cys Val Thr Asp Ser Gly Val Val Tyr Ser Val Gly
        275                 280                 285
Met Gln Trp Leu Lys Thr Gln Gly Asn Lys Gln Met Leu Cys Thr Cys
    290                 295                 300
Leu Gly Asn Gly Val Ser Cys Gln Glu Thr Ala Val Thr Gln Thr Tyr
305                 310                 315                 320
Gly Gly Asn Ser Asn Gly Glu Pro Cys Val Leu Pro Phe Thr Tyr Asn
                325                 330                 335
Gly Arg Thr Phe Tyr Ser Cys Thr Thr Glu Gly Arg Gln Asp Gly His
            340                 345                 350
Leu Trp Cys Ser Thr Thr Ser Asn Tyr Glu Gln Asp Gln Lys Tyr Ser
        355                 360                 365
Phe Cys Thr Asp His Thr Val Leu Val Gln Thr Gln Gly Gly Asn Ser
370                 375                 380
Asn Gly Ala Leu Cys His Phe Pro Phe Leu Tyr Asn Asn His Asn Tyr
385                 390                 395                 400
Thr Asp Cys Thr Ser Glu Gly Arg Arg Asp Asn Met Lys Trp Cys Gly
            405                 410                 415
Thr Thr Gln Asn Tyr Asp Ala Asp Gln Lys Phe Gly Phe Cys Pro Met
        420                 425                 430
Ala Ala His Glu Glu Ile Cys Thr Thr Asn Glu Gly Val Met Tyr Arg
435                 440                 445
Ile Gly Asp Gln Trp Asp Lys Gln His Asp Met Gly His Met Met Arg
450                 455                 460
Cys Thr Cys Val Gly Asn Gly Arg Gly Glu Trp Thr Cys Tyr Ala Tyr
465                 470                 475                 480
Ser Gln Leu Arg Asp Gln Cys Ile Val Asp Asp Ile Thr Tyr Asn Val
            485                 490                 495
Asn Asp Thr Phe His Lys Arg His Glu Glu Gly His Met Leu Asn Cys
        500                 505                 510
Thr Cys Phe Gly Gln Gly Arg Gly Arg Trp Lys Cys Asp Pro Val Asp
    515                 520                 525
Gln Cys Gln Asp Ser Glu Thr Gly Thr Phe Tyr Gln Ile Gly Asp Ser
```

-continued

|     | 530 |     |     |     | 535 |     |     |     | 540 |     |     |     |
| --- | --- | --- | --- | --- | --- | --- | --- | --- | --- | --- | --- | --- |
| Trp 545 | Glu | Lys | Tyr | Val | His 550 | Gly | Val | Arg | Tyr | Gln 555 | Cys | Tyr | Cys | Tyr | Gly 560 |
| Arg | Gly | Ile | Gly | Glu 565 | Trp | His | Cys | Gln | Pro 570 | Leu | Gln | Thr | Tyr | Arg 575 | Ser |
| Ser | Ser | Gly | Pro 580 | Val | Glu | Val | Phe | Ile 585 | Thr | Glu | Thr | Pro | Ser 590 | Gln | Pro |
| Asn | Ser | His 595 | Pro | Ile | Gln | Pro | Asn 600 | Ala | Pro | Gln | Pro | Ser 605 | His | Ile | Ser |
| Lys | Tyr 610 | Ile | Leu | Arg | Trp | Arg 615 | Pro | Lys | Asn | Ser | Val 620 | Gly | Arg | Trp | Lys |
| Glu 625 | Ala | Thr | Ile | Pro | Gly 630 | His | Leu | Asn | Ser | Tyr 635 | Thr | Ile | Lys | Gly | Leu 640 |
| Lys | Pro | Gly | Val | Val 645 | Tyr | Glu | Gly | Gln | Leu 650 | Ile | Ser | Ile | Gln | Gln 655 | Tyr |
| Gly | His | Gln | Glu 660 | Val | Thr | Arg | Phe | Asp 665 | Phe | Thr | Thr | Thr | Ser 670 | Thr | Ser |
| Thr | Pro | Val 675 | Thr | Ser | Asn | Thr | Val 680 | Thr | Gly | Glu | Thr | Thr 685 | Pro | Phe | Ser |
| Pro | Leu 690 | Val | Ala | Thr | Ser | Glu 695 | Ser | Val | Thr | Glu | Ile 700 | Thr | Ala | Ser | Ser |
| Phe 705 | Val | Val | Ser | Trp | Val 710 | Ser | Ala | Ser | Asp | Thr 715 | Val | Ser | Gly | Phe | Arg 720 |
| Val | Glu | Tyr | Glu | Leu 725 | Ser | Glu | Glu | Gly | Asp 730 | Glu | Pro | Gln | Tyr | Leu 735 | Asp |
| Leu | Pro | Ser | Thr 740 | Ala | Thr | Ser | Val | Asn 745 | Ile | Pro | Asp | Leu | Leu 750 | Pro | Gly |
| Arg | Lys | Tyr 755 | Ile | Val | Asn | Val | Tyr 760 | Gln | Ile | Ser | Glu | Asp 765 | Gly | Glu | Gln |
| Ser | Leu 770 | Ile | Leu | Ser | Thr | Ser 775 | Gln | Thr | Thr | Ala | Pro 780 | Asp | Ala | Pro | Pro |
| Asp 785 | Pro | Thr | Val | Asp | Gln 790 | Val | Asp | Asp | Thr | Ser 795 | Ile | Val | Val | Arg | Trp 800 |
| Ser | Arg | Pro | Gln | Ala 805 | Pro | Ile | Thr | Gly | Tyr 810 | Arg | Ile | Val | Tyr | Ser 815 | Pro |
| Ser | Val | Glu | Glu 820 | Ser | Ser | Thr | Glu | Leu 825 | Asn | Leu | Pro | Glu | Thr 830 | Ala | Asn |
| Ser | Val | Thr 835 | Leu | Ser | Asp | Leu | Gln 840 | Pro | Gly | Val | Gln | Tyr 845 | Asn | Ile | Thr |
| Ile | Tyr 850 | Ala | Val | Glu | Glu | Asn 855 | Gln | Glu | Ser | Thr | Pro 860 | Val | Val | Ile | Gln |
| Gln 865 | Glu | Thr | Thr | Gly | Thr 870 | Pro | Arg | Ser | Asp | Thr 875 | Val | Pro | Ser | Pro | Arg 880 |
| Asp | Leu | Gln | Phe | Val 885 | Glu | Val | Thr | Asp | Val 890 | Lys | Val | Thr | Ile | Met 895 | Trp |
| Thr | Pro | Pro | Glu 900 | Ser | Ala | Val | Thr | Gly 905 | Tyr | Arg | Val | Asp | Val 910 | Ile | Pro |
| Val | Asn | Leu 915 | Pro | Gly | Glu | His | Gly 920 | Gln | Arg | Leu | Pro | Ile 925 | Ser | Arg | Asn |
| Thr | Phe 930 | Ala | Glu | Val | Thr | Gly 935 | Leu | Ser | Pro | Gly | Val 940 | Thr | Tyr | Tyr | Phe |
| Lys 945 | Val | Phe | Ala | Val | Ser 950 | His | Gly | Arg | Glu | Ser 955 | Lys | Pro | Leu | Thr | Ala 960 |

Gln Gln Thr Thr Lys Leu Asp Ala Pro Thr Asn Leu Gln Phe Val Asn
        965                 970                 975

Glu Thr Asp Ser Thr Val Leu Val Arg Trp Thr Pro Pro Arg Ala Gln
        980                 985                 990

Ile Thr Gly Tyr Arg Leu Thr Val Gly Leu Thr Arg Arg Gly Gln Pro
        995                 1000                1005

Arg Gln Tyr Asn Val Gly Pro Ser Val Ser Lys Tyr Pro Leu Arg Asn
    1010                1015                1020

Leu Gln Pro Ala Ser Glu Tyr Thr Val Ser Leu Val Ala Ile Lys Gly
1025                1030                1035                1040

Asn Gln Glu Ser Pro Lys Ala Thr Gly Val Phe Thr Thr Leu Gln Pro
            1045                1050                1055

Gly Ser Ser Ile Pro Pro Tyr Asn Thr Glu Val Thr Glu Thr Thr Ile
        1060                1065                1070

Val Ile Thr Trp Thr Pro Ala Pro Arg Ile Gly Phe Lys Leu Gly Val
        1075                1080                1085

Arg Pro Ser Gln Gly Gly Glu Ala Pro Arg Glu Val Thr Ser Asp Ser
        1090                1095                1100

Gly Ser Ile Val Val Ser Gly Leu Thr Pro Gly Val Glu Tyr Val Tyr
1105                1110                1115                1120

Thr Ile Gln Val Leu Arg Asp Gly Gln Glu Arg Asp Ala Pro Ile Val
            1125                1130                1135

Asn Lys Val Val Thr Pro Leu Ser Pro Pro Thr Asn Leu His Leu Glu
        1140                1145                1150

Ala Asn Pro Asp Thr Gly Val Leu Thr Val Ser Trp Glu Arg Ser Thr
        1155                1160                1165

Thr Pro Asp Ile Thr Gly Tyr Arg Ile Thr Thr Thr Pro Thr Asn Gly
        1170                1175                1180

Gln Gln Gly Asn Ser Leu Glu Glu Val Val His Ala Asp Gln Ser Ser
1185                1190                1195                1200

Cys Thr Phe Asp Asn Leu Ser Pro Gly Leu Glu Tyr Asn Val Ser Val
            1205                1210                1215

Tyr Thr Val Lys Asp Asp Lys Glu Ser Val Pro Ile Ser Asp Thr Ile
        1220                1225                1230

Ile Pro Ala Val Pro Pro Pro Thr Asp Leu Arg Phe Thr Asn Ile Gly
        1235                1240                1245

Pro Asp Thr Met Arg Val Thr Trp Ala Pro Pro Ser Ile Asp Leu
        1250                1255                1260

Thr Asn Phe Leu Val Arg Tyr Ser Pro Val Lys Asn Glu Glu Asp Val
1265                1270                1275                1280

Ala Glu Leu Ser Ile Ser Pro Ser Asp Asn Ala Val Val Leu Thr Asn
            1285                1290                1295

Leu Leu Pro Gly Thr Glu Tyr Val Val Ser Val Ser Ser Val Tyr Glu
        1300                1305                1310

Gln His Glu Ser Thr Pro Leu Arg Gly Arg Gln Lys Thr Gly Leu Asp
        1315                1320                1325

Ser Pro Thr Gly Ile Asp Phe Ser Asp Ile Thr Ala Asn Ser Phe Thr
        1330                1335                1340

Val His Trp Ile Ala Pro Arg Ala Thr Ile Thr Gly Tyr Arg Ile Arg
1345                1350                1355                1360

His His Pro Glu His Phe Ser Gly Arg Pro Arg Glu Asp Arg Val Pro
            1365                1370                1375

His Ser Arg Asn Ser Ile Thr Leu Thr Asn Leu Thr Pro Gly Thr Glu
        1380                1385                1390

-continued

```
Tyr  Val  Val  Ser  Ile  Val  Ala  Leu  Asn  Gly  Arg  Glu  Glu  Ser  Pro  Leu
          1395                1400                1405
Leu  Ile  Gly  Gln  Gln  Ser  Thr  Val  Ser  Asp  Val  Pro  Arg  Asp  Leu  Glu
1410                     1415                     1420
Val  Val  Ala  Ala  Thr  Pro  Thr  Ser  Leu  Leu  Ile  Ser  Trp  Asp  Ala  Pro
1425                     1430                     1435                     1440
Ala  Val  Thr  Val  Arg  Tyr  Tyr  Arg  Ile  Thr  Tyr  Gly  Glu  Thr  Gly  Gly
                    1445                     1450                     1455
Asn  Ser  Pro  Val  Gln  Glu  Phe  Thr  Val  Pro  Gly  Ser  Lys  Ser  Thr  Ala
               1460                     1465                     1470
Thr  Ile  Ser  Gly  Leu  Lys  Pro  Gly  Val  Asp  Tyr  Thr  Ile  Thr  Val  Tyr
          1475                     1480                     1485
Ala  Val  Thr  Gly  Arg  Gly  Asp  Ser  Pro  Ala  Ser  Ser  Lys  Pro  Ile  Ser
     1490                     1495                     1500
Ile  Asn  Tyr  Arg  Thr  Glu  Ile  Asp  Lys  Pro  Ser  Gln  Met  Gln  Val  Thr
1505                     1510                     1515                     1520
Asp  Val  Gln  Asp  Asn  Ser  Ile  Ser  Val  Lys  Trp  Leu  Pro  Ser  Ser  Ser
                    1525                     1530                     1535
Pro  Val  Thr  Gly  Tyr  Arg  Val  Thr  Thr  Thr  Pro  Lys  Asn  Gly  Pro  Gly
               1540                     1545                     1550
Pro  Thr  Lys  Thr  Lys  Thr  Ala  Gly  Pro  Asp  Gln  Thr  Glu  Met  Thr  Ile
          1555                     1560                     1565
Glu  Gly  Leu  Gln  Pro  Thr  Val  Glu  Tyr  Val  Val  Ser  Val  Tyr  Ala  Gln
     1570                     1575                     1580
Asn  Pro  Ser  Gly  Glu  Ser  Gln  Pro  Leu  Val  Gln  Thr  Ala  Val  Thr  Thr
1585                     1590                     1595                     1600
Ile  Pro  Ala  Pro  Thr  Asp  Leu  Lys  Phe  Thr  Gln  Val  Thr  Pro  Thr  Ser
                    1605                     1610                     1615
Leu  Ser  Ala  Gln  Trp  Thr  Pro  Pro  Asp  Val  Gln  Leu  Thr  Gly  Tyr  Arg
               1620                     1625                     1630
Val  Arg  Val  Thr  Pro  Lys  Gln  Lys  Thr  Gly  Pro  Met  Lys  Glu  Ile  Asn
          1635                     1640                     1645
Leu  Ala  Pro  Asp  Ser  Ser  Ser  Val  Val  Val  Ser  Gly  Leu  Met  Val  Ala
     1650                     1655                     1660
Thr  Lys  Tyr  Glu  Val  Ser  Val  Tyr  Ala  Leu  Lys  Asp  Thr  Leu  Thr  Ser
1665                     1670                     1675                     1680
Arg  Pro  Ala  Gln  Gly  Val  Val  Thr  Thr  Leu  Glu  Asn  Val  Ser  Pro  Pro
                    1685                     1690                     1695
Arg  Arg  Ala  Arg  Val  Thr  Asp  Ala  Thr  Glu  Thr  Thr  Ile  Thr  Ile  Ser
               1700                     1705                     1710
Trp  Arg  Thr  Lys  Thr  Glu  Thr  Ile  Thr  Gly  Phe  Gln  Val  Asp  Ala  Val
          1715                     1720                     1725
Pro  Ala  Asn  Gly  Gln  Thr  Pro  Ile  Gln  Arg  Thr  Ile  Lys  Pro  Asp  Val
     1730                     1735                     1740
Arg  Ser  Tyr  Thr  Ile  Thr  Gly  Leu  Gln  Pro  Gly  Thr  Asp  Tyr  Lys  Ile
1745                     1750                     1755                     1760
Tyr  Leu  Tyr  Thr  Leu  Asn  Asp  Asn  Ala  Arg  Ser  Ser  Pro  Val  Val  Ile
                    1765                     1770                     1775
Asp  Ala  Ser  Thr  Ala  Ile  Asp  Ala  Pro  Ser  Asn  Leu  Arg  Phe  Leu  Ala
               1780                     1785                     1790
Thr  Thr  Pro  Asn  Ser  Leu  Leu  Val  Ser  Trp  Gln  Pro  Pro  Arg  Ala  Arg
          1795                     1800                     1805
Ile  Thr  Gly  Tyr  Ile  Ile  Lys  Tyr  Glu  Lys  Pro  Gly  Ser  Pro  Pro  Arg
```

```
        1810                    1815                    1820
Glu  Val  Val  Pro  Arg  Pro  Arg  Pro  Gly  Val  Thr  Glu  Ala  Thr  Ile  Thr
1825                    1830                    1835                    1840
Gly  Leu  Glu  Pro  Gly  Thr  Glu  Tyr  Thr  Ile  Tyr  Val  Ile  Ala  Leu  Lys
                        1845                    1850                    1855
Asn  Asn  Gln  Lys  Ser  Glu  Pro  Leu  Ile  Gly  Arg  Lys  Lys  Thr  Asp  Glu
                        1860                    1865                    1870
Leu  Pro  Gln  Leu  Val  Thr  Leu  Pro  His  Pro  Asn  Leu  His  Gly  Pro  Glu
                        1875                    1880                    1885
Ile  Leu  Asp  Val  Pro  Ser  Thr  Val  Gln  Lys  Thr  Pro  Phe  Val  Thr  His
            1890                    1895                    1900
Pro  Gly  Tyr  Asp  Thr  Gly  Asn  Gly  Ile  Gln  Leu  Pro  Gly  Thr  Ser  Gly
1905                    1910                    1915                    1920
Gln  Gln  Pro  Ser  Val  Gly  Gln  Gln  Met  Ile  Phe  Glu  Glu  His  Gly  Phe
                        1925                    1930                    1935
Arg  Arg  Thr  Thr  Pro  Pro  Thr  Thr  Ala  Thr  Pro  Ile  Arg  His  Arg  Pro
                        1940                    1945                    1950
Arg  Pro  Tyr  Pro  Pro  Asn  Val  Ala  Leu  Ser  Gln  Thr  Thr  Ile  Ser  Trp
            1955                    1960                    1965
Ala  Pro  Phe  Gln  Asp  Thr  Ser  Glu  Tyr  Ile  Ile  Ser  Cys  His  Pro  Val
            1970                    1975                    1980
Gly  Thr  Asp  Glu  Glu  Pro  Leu  Gln  Phe  Arg  Val  Pro  Gly  Thr  Ser  Thr
1985                    1990                    1995                    2000
Ser  Ala  Thr  Leu  Thr  Gly  Leu  Thr  Arg  Gly  Ala  Thr  Tyr  Asn  Ile  Ile
                        2005                    2010                    2015
Val  Glu  Ala  Leu  Lys  Asp  Gln  Gln  Arg  His  Lys  Val  Arg  Glu  Glu  Val
                        2020                    2025                    2030
Val  Thr  Val  Gly  Asn  Ser  Val  Asn  Gln  Gly  Leu  Asn  Gln  Pro  Thr  Asp
            2035                    2040                    2045
Asp  Ser  Cys  Phe  Asp  Pro  Tyr  Thr  Val  Ser  His  Tyr  Ala  Val  Gly  Asp
            2050                    2055                    2060
Glu  Trp  Glu  Arg  Met  Ser  Glu  Ser  Gly  Phe  Lys  Leu  Leu  Cys  Gln  Cys
2065                    2070                    2075                    2080
Leu  Gly  Phe  Gly  Ser  Gly  His  Phe  Arg  Cys  Asp  Ser  Ser  Arg  Trp  Cys
                        2085                    2090                    2095
His  Asp  Asn  Gly  Val  Asn  Tyr  Lys  Ile  Gly  Glu  Lys  Trp  Asp  Arg  Gln
                        2100                    2105                    2110
Gly  Glu  Asn  Gly  Gln  Met  Met  Ser  Cys  Thr  Cys  Leu  Gly  Asn  Gly  Lys
                        2115                    2120                    2125
Gly  Glu  Phe  Lys  Cys  Asp  Pro  His  Glu  Ala  Thr  Cys  Tyr  Asp  Asp  Gly
            2130                    2135                    2140
Lys  Thr  Tyr  His  Val  Gly  Glu  Gln  Trp  Gln  Lys  Glu  Tyr  Leu  Gly  Ala
2145                    2150                    2155                    2160
Ile  Cys  Ser  Cys  Thr  Cys  Phe  Gly  Gly  Gln  Arg  Gly  Trp  Arg  Cys  Asp
                        2165                    2170                    2175
Asn  Cys  Arg  Arg  Pro  Gly  Gly  Glu  Pro  Ser  Pro  Glu  Gly  Thr  Thr  Gly
                        2180                    2185                    2190
Gln  Ser  Tyr  Asn  Gln  Tyr  Ser  Gln  Arg  Tyr  His  Gln  Arg  Thr  Asn  Thr
            2195                    2200                    2205
Asn  Val  Asn  Cys  Pro  Ile  Glu  Cys  Phe  Met  Pro  Leu  Asp  Val  Gln  Ala
            2210                    2215                    2220
Asp  Arg  Glu  Asp  Ser  Arg  Glu
2225                    2230
```

(2) INFORMATION FOR SEQ ID NO:17:

(i) SEQUENCE CHARACTERISTICS:
        (A) LENGTH: 1236 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..1236
        (D) OTHER INFORMATION: /function="human mature
            urokinase- type plasminogen activator (uPA)"

(ix) FEATURE:
        (A) NAME/KEY: primer_bind
        (B) LOCATION: 13..47
        (D) OTHER INFORMATION: /standard_name= "PCR primer binding
            site"

(ix) FEATURE:
        (A) NAME/KEY: primer_bind
        (B) LOCATION: 376..418
        (D) OTHER INFORMATION: /standard_name= "PCR primer binding
            site"

(xi) SEQUENCE DESCRIPTION: SEQ ID NO:17:

```
AGC AAT GAA CTT CAT CAA GTT CCA TCG AAC TGT GAC TGT CTA AAT GGA        48
Ser Asn Glu Leu His Gln Val Pro Ser Asn Cys Asp Cys Leu Asn Gly
 1               5                  10                  15

GGA ACA TGT GTG TCC AAC AAG TAC TTC TCC AAC ATT CAC TGG TGC AAC        96
Gly Thr Cys Val Ser Asn Lys Tyr Phe Ser Asn Ile His Trp Cys Asn
                20                  25                  30

TGC CCA AAG AAA TTC GGA GGG CAG CAC TGT GAA ATA GAT AAG TCA AAA       144
Cys Pro Lys Lys Phe Gly Gly Gln His Cys Glu Ile Asp Lys Ser Lys
            35                  40                  45

ACC TGC TAT GAG GGG AAT GGT CAC TTT TAC CGA GGA AAG GCC AGC ACT       192
Thr Cys Tyr Glu Gly Asn Gly His Phe Tyr Arg Gly Lys Ala Ser Thr
        50                  55                  60

GAC ACC ATG GGC CGG CCC TGC CTG CCC TGG AAC TCT GCC ACT GTC CTT       240
Asp Thr Met Gly Arg Pro Cys Leu Pro Trp Asn Ser Ala Thr Val Leu
 65                  70                  75                  80

CAG CAA ACG TAC CAT GCC CAC AGA TCT GAT GCT CTT CAG CTG GGC CTG       288
Gln Gln Thr Tyr His Ala His Arg Ser Asp Ala Leu Gln Leu Gly Leu
                85                  90                  95

GGG AAA CAT AAT TAC TGC AGG AAC CCA GAC AAC CGG AGG CGA CCC TGG       336
Gly Lys His Asn Tyr Cys Arg Asn Pro Asp Asn Arg Arg Arg Pro Trp
               100                 105                 110

TGC TAT GTG CAG GTG GGC CTA AAG CCG CTT GTC CAA GAG TGC ATG GTG       384
Cys Tyr Val Gln Val Gly Leu Lys Pro Leu Val Gln Glu Cys Met Val
           115                 120                 125

CAT GAC TGC GCA GAT GGA AAA AAG CCC TCC TCT CCT CCA GAA GAA TTA       432
His Asp Cys Ala Asp Gly Lys Lys Pro Ser Ser Pro Pro Glu Glu Leu
       130                 135                 140

AAA TTT CAG TGT GGC CAA AAG ACT CTG AGG CCC CGC TTT AAG ATT ATT       480
Lys Phe Gln Cys Gly Gln Lys Thr Leu Arg Pro Arg Phe Lys Ile Ile
145                 150                 155                 160

GGG GGA GAA TTC ACC ACC ATC GAG AAC CAG CCC TGG TTT GCG GCC ATC       528
Gly Gly Glu Phe Thr Thr Ile Glu Asn Gln Pro Trp Phe Ala Ala Ile
```

| | | | | | | | | | | | | | | | | |
|---|---|---|---|---|---|---|---|---|---|---|---|---|---|---|---|---|
| | | | | 165 | | | | | 170 | | | | | 175 | | |
| TAC | AGG | AGG | CAC | CGG | GGG | GGC | TCT | GTC | ACC | TAC | GTG | TGT | GGA | GGC | AGC | 576 |
| Tyr | Arg | Arg | His | Arg | Gly | Gly | Ser | Val | Thr | Tyr | Val | Cys | Gly | Gly | Ser | |
| | | | 180 | | | | | 185 | | | | | 190 | | | |
| CTC | ATC | AGC | CCT | TGC | TGG | GTG | ATC | AGC | GCC | ACA | CAC | TGC | TTC | ATT | GAT | 624 |
| Leu | Ile | Ser | Pro | Cys | Trp | Val | Ile | Ser | Ala | Thr | His | Cys | Phe | Ile | Asp | |
| | | 195 | | | | | 200 | | | | | 205 | | | | |
| TAC | CCA | AAG | AAG | GAG | GAC | TAC | ATC | GTC | TAC | CTG | GGT | CGC | TCA | AGG | CTT | 672 |
| Tyr | Pro | Lys | Lys | Glu | Asp | Tyr | Ile | Val | Tyr | Leu | Gly | Arg | Ser | Arg | Leu | |
| | 210 | | | | | 215 | | | | | 220 | | | | | |
| AAC | TCC | AAC | ACG | CAA | GGG | GAG | ATG | AAG | TTT | GAG | GTG | GAA | AAC | CTC | ATC | 720 |
| Asn | Ser | Asn | Thr | Gln | Gly | Glu | Met | Lys | Phe | Glu | Val | Glu | Asn | Leu | Ile | |
| 225 | | | | | 230 | | | | | 235 | | | | | 240 | |
| CTA | CAC | AAG | GAC | TAC | AGC | GCT | GAC | ACG | CTT | GCT | CAC | CAC | AAC | GAC | ATT | 768 |
| Leu | His | Lys | Asp | Tyr | Ser | Ala | Asp | Thr | Leu | Ala | His | His | Asn | Asp | Ile | |
| | | | | 245 | | | | | 250 | | | | | 255 | | |
| GCC | TTG | CTG | AAG | ATC | CGT | TCC | AAG | GAG | GGC | AGG | TGT | GCG | CAG | CCA | TCC | 816 |
| Ala | Leu | Leu | Lys | Ile | Arg | Ser | Lys | Glu | Gly | Arg | Cys | Ala | Gln | Pro | Ser | |
| | | | 260 | | | | | 265 | | | | | 270 | | | |
| CGG | ACT | ATA | CAG | ACC | ATC | TGC | CTG | CCC | TCG | ATG | TAT | AAC | GAT | CCC | CAG | 864 |
| Arg | Thr | Ile | Gln | Thr | Ile | Cys | Leu | Pro | Ser | Met | Tyr | Asn | Asp | Pro | Gln | |
| | | 275 | | | | | 280 | | | | | 285 | | | | |
| TTT | GGC | ACA | AGC | TGT | GAG | ATC | ACT | GGC | TTT | GGA | AAA | GAG | AAT | TCT | ACC | 912 |
| Phe | Gly | Thr | Ser | Cys | Glu | Ile | Thr | Gly | Phe | Gly | Lys | Glu | Asn | Ser | Thr | |
| | 290 | | | | | 295 | | | | | 300 | | | | | |
| GAC | TAT | CTC | TAT | CCG | GAG | CAG | CTG | AAA | ATG | ACT | GTT | GTG | AAG | CTG | ATT | 960 |
| Asp | Tyr | Leu | Tyr | Pro | Glu | Gln | Leu | Lys | Met | Thr | Val | Val | Lys | Leu | Ile | |
| 305 | | | | | 310 | | | | | 315 | | | | | 320 | |
| TCC | CAC | CGG | GAG | TGT | CAG | CAG | CCC | CAC | TAC | TAC | GGC | TCT | GAA | GTC | ACC | 1008 |
| Ser | His | Arg | Glu | Cys | Gln | Gln | Pro | His | Tyr | Tyr | Gly | Ser | Glu | Val | Thr | |
| | | | | 325 | | | | | 330 | | | | | 335 | | |
| ACC | AAA | ATG | CTA | TGT | GCT | GCT | GAC | CCC | CAA | TGG | AAA | ACA | GAT | TCC | TGC | 1056 |
| Thr | Lys | Met | Leu | Cys | Ala | Ala | Asp | Pro | Gln | Trp | Lys | Thr | Asp | Ser | Cys | |
| | | | 340 | | | | | 345 | | | | | 350 | | | |
| CAG | GGA | GAC | TCA | GGG | GGA | CCC | CTC | GTC | TGT | TCC | CTC | CAA | GGC | CGC | ATG | 1104 |
| Gln | Gly | Asp | Ser | Gly | Gly | Pro | Leu | Val | Cys | Ser | Leu | Gln | Gly | Arg | Met | |
| | | 355 | | | | | 360 | | | | | 365 | | | | |
| ACT | TTG | ACT | GGA | ATT | GTG | AGC | TGG | GGC | CGT | GGA | TGT | GCC | CTG | AAG | GAC | 1152 |
| Thr | Leu | Thr | Gly | Ile | Val | Ser | Trp | Gly | Arg | Gly | Cys | Ala | Leu | Lys | Asp | |
| | 370 | | | | | 375 | | | | | 380 | | | | | |
| AAG | CCA | GGC | GTC | TAC | ACG | AGA | GTC | TCA | CAC | TTC | TTA | CCC | TGG | ATC | CGC | 1200 |
| Lys | Pro | Gly | Val | Tyr | Thr | Arg | Val | Ser | His | Phe | Leu | Pro | Trp | Ile | Arg | |
| 385 | | | | | 390 | | | | | 395 | | | | | 400 | |
| AGT | CAC | ACC | AAG | GAA | GAG | AAT | GGC | CTG | GCC | CTC | TGA | | | | | 1236 |
| Ser | His | Thr | Lys | Glu | Glu | Asn | Gly | Leu | Ala | Leu | | | | | | |
| | | | | 405 | | | | | 410 | | | | | | | |

( 2 ) INFORMATION FOR SEQ ID NO:18:

( i ) SEQUENCE CHARACTERISTICS:
        ( A ) LENGTH: 411 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| | | | | | | | | | | | | | | |
|---|---|---|---|---|---|---|---|---|---|---|---|---|---|---|
| Ser | Asn | Glu | Leu | His | Gln | Val | Pro | Ser | Asn | Cys | Asp | Cys | Leu | Asn | Gly |
| 1 | | | | 5 | | | | | 10 | | | | | 15 | |
| Gly | Thr | Cys | Val | Ser | Asn | Lys | Tyr | Phe | Ser | Asn | Ile | His | Trp | Cys | Asn |
| | | | 20 | | | | | 25 | | | | | 30 | | |

-continued

| | | | | | | | | | | | | | |
|---|---|---|---|---|---|---|---|---|---|---|---|---|---|
| Cys | Pro | Lys 35 | Lys | Phe | Gly | Gly 40 | Gln | His | Cys | Glu | Ile 45 | Asp | Lys | Ser | Lys |
| Thr | Cys 50 | Tyr | Glu | Gly | Asn 55 | Gly | His | Phe | Tyr | Arg 60 | Gly | Lys | Ala | Ser | Thr |
| Asp 65 | Thr | Met | Gly | Arg | Pro 70 | Cys | Leu | Pro | Trp | Asn 75 | Ser | Ala | Thr | Val | Leu 80 |
| Gln | Gln | Thr | Tyr | His 85 | Ala | His | Arg | Ser | Asp 90 | Ala | Leu | Gln | Leu | Gly 95 | Leu |
| Gly | Lys | His | Asn 100 | Tyr | Cys | Arg | Asn | Pro 105 | Asp | Asn | Arg | Arg | Arg 110 | Pro | Trp |
| Cys | Tyr | Val 115 | Gln | Val | Gly | Leu | Lys 120 | Pro | Leu | Val | Gln | Glu 125 | Cys | Met | Val |
| His | Asp 130 | Cys | Ala | Asp | Gly | Lys 135 | Lys | Pro | Ser | Ser | Pro 140 | Pro | Glu | Glu | Leu |
| Lys 145 | Phe | Gln | Cys | Gly | Gln 150 | Lys | Thr | Leu | Arg | Pro 155 | Arg | Phe | Lys | Ile | Ile 160 |
| Gly | Gly | Glu | Phe | Thr 165 | Thr | Ile | Glu | Asn | Gln 170 | Pro | Trp | Phe | Ala | Ala 175 | Ile |
| Tyr | Arg | Arg | His 180 | Arg | Gly | Gly | Ser | Val 185 | Thr | Tyr | Val | Cys | Gly 190 | Gly | Ser |
| Leu | Ile | Ser 195 | Pro | Cys | Trp | Val | Ile 200 | Ser | Ala | Thr | His | Cys 205 | Phe | Ile | Asp |
| Tyr | Pro 210 | Lys | Lys | Glu | Asp | Tyr 215 | Ile | Val | Tyr | Leu | Gly 220 | Arg | Ser | Arg | Leu |
| Asn 225 | Ser | Asn | Thr | Gln | Gly 230 | Glu | Met | Lys | Phe | Glu 235 | Val | Glu | Asn | Leu | Ile 240 |
| Leu | His | Lys | Asp | Tyr 245 | Ser | Ala | Asp | Thr | Leu 250 | Ala | His | His | Asn | Asp 255 | Ile |
| Ala | Leu | Leu | Lys 260 | Ile | Arg | Ser | Lys | Glu 265 | Gly | Arg | Cys | Ala | Gln 270 | Pro | Ser |
| Arg | Thr | Ile 275 | Gln | Thr | Ile | Cys | Leu 280 | Pro | Ser | Met | Tyr | Asn 285 | Asp | Pro | Gln |
| Phe | Gly 290 | Thr | Ser | Cys | Glu | Ile 295 | Thr | Gly | Phe | Gly | Lys 300 | Glu | Asn | Ser | Thr |
| Asp 305 | Tyr | Leu | Tyr | Pro | Glu 310 | Gln | Leu | Lys | Met | Thr 315 | Val | Val | Lys | Leu | Ile 320 |
| Ser | His | Arg | Glu | Cys 325 | Gln | Gln | Pro | His | Tyr 330 | Tyr | Gly | Ser | Glu | Val 335 | Thr |
| Thr | Lys | Met | Leu 340 | Cys | Ala | Ala | Asp | Pro 345 | Gln | Trp | Lys | Thr | Asp 350 | Ser | Cys |
| Gln | Gly | Asp 355 | Ser | Gly | Gly | Pro | Leu 360 | Val | Cys | Ser | Leu | Gln 365 | Gly | Arg | Met |
| Thr | Leu 370 | Thr | Gly | Ile | Val | Ser 375 | Trp | Gly | Arg | Gly | Cys 380 | Ala | Leu | Lys | Asp |
| Lys 385 | Pro | Gly | Val | Tyr | Thr 390 | Arg | Val | Ser | His | Phe 395 | Leu | Pro | Trp | Ile | Arg 400 |
| Ser | His | Thr | Lys | Glu 405 | Glu | Asn | Gly | Leu | Ala 410 | Leu | | | | | |

( 2 ) INFORMATION FOR SEQ ID NO:19:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear (i i) MOLECULE TYPE: DNA (genomic)

(i i i) HYPOTHETICAL: NO (i v) ANTI-SENSE: NO (i x) FEATURE:
    (A) NAME/KEY: CDS
    (B) LOCATION: 6..11
    (D) OTHER INFORMATION: /function="encodes first two amino
        acids of mature HSA"

(i x) FEATURE:
    (A) NAME/KEY: misc_feature
    (B) LOCATION: 6..8
    (D) OTHER INFORMATION: /function="overlaps XhoI site"

(x i) SEQUENCE DESCRIPTION: SEQ ID NO:19:

```
CTCGA GAT GCA                                                        11
      Asp Ala
       1
```

(2) INFORMATION FOR SEQ ID NO:20:

(i) SEQUENCE CHARACTERISTICS:
        (A) LENGTH: 2 amino acids
        (B) TYPE: amino acid
        (D) TOPOLOGY: linear (i i) MOLECULE TYPE: protein (x i) SEQUENCE DESCRIPTION: SEQ ID NO:20:

```
Asp Ala
 1
```

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (i x) FEATURE:
        (A) NAME/KEY: misc_feature
        (B) LOCATION: 1..20
        (D) OTHER INFORMATION: /function="mutagenic primer used to
            create a XhoI site in pDBDF6"

(x i) SEQUENCE DESCRIPTION: SEQ ID NO:21:

```
CCAAAGCTCG AGGAACTTCG                                                20
```

(2) INFORMATION FOR SEQ ID NO:22:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (i x) FEATURE:

```
            ( A ) NAME/KEY: CDS
            ( B ) LOCATION: 1..12
            ( D ) OTHER INFORMATION: /function="Region encoding
                 cleavage recognition site for Factor X"

( x i ) SEQUENCE DESCRIPTION: SEQ ID NO:22:

ATT  GAA  GGT  AGA                                                              1 2
Ile  Glu  Gly  Arg
  1

( 2 ) INFORMATION FOR SEQ ID NO:23:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: protein ( x i ) SEQUENCE DESCRIPTION: SEQ ID NO:23:

Ile  Glu  Gly  Arg
  1
```

POLYPEPTIDES

RELATED APPLICATIONS

This is a continuation of application Ser. No. 07/847,975 filed Mar. 6, 1992, now abandoned, which is a continuation-in-part of application Ser. No. 07/775,952, filed Oct. 29, 1992, now abandoned.

BACKGROUND OF THE INVENTION

The present invention relates to fusion polypeptides where two individual polypeptides or parts thereof are fused to form a single amino acid chain. Such fusion may arise from the expression of a single continuous coding sequence formed by recombinant DNA techniques.

PRIOR ART

Fusion polypeptides are known, for example those where a polypeptide which is the ultimately desired product of the process is expressed with an N-terminal "leader sequence" which encourages or allows secretion of the polypeptide from the cell. An example is disclosed in EP-A-116 201 (Chiron). A glucoamylase-interleukin 6 fusion, cleavable by an Aspergillus enzyme related to the *S. cerevisiae* KEX2-encoded protease yscF, was expressed in Aspergillus (Contreras et al 1991).

Human serum albumin (HSA) is a known protein found in the blood. EP-A-147 198 (Delta Biotechnology) discloses its expression in a transformed host, in this case yeast. EP-A-322 094 discloses N-terminal fragments of HSA, namely those consisting of residues 1–n where n is 369 to 419, which have therapeutic utility. The application also mentions the possibility of fusing the C-terminal residue of such molecules to other, unnamed, polypeptides.

SUMMARY OF THE INVENTION

One aspect of the present invention provides a fusion polypeptide comprising: as at least part of the N-terminal portion thereof, an N-terminal polypeptide portion of HSA or a variant thereof; and, as at least part of the C-terminal portion thereof, a second polypeptide; wherein, when the said N-terminal portion of HSA is the 1–n portion where n is 369 to 419 or a variant thereof, said second polypeptide is selected from the group consisting of (a) the 585 to 1578 portion of human fibronectin or a variant thereof; (b) the 1 to 368 portion of CD4 or a variant thereof; (c) platelet derived growth factor or a variant thereof; (d) transforming growth factor β or a variant thereof; (e) the 1–261 portion of mature human plasma fibronectin or a variant thereof; (f) the 278–578 portion of mature human plasma fibronectin or a variant thereof; (g) the 1–272 portion of mature human von Willebrand's Factor or a variant thereof; and (h) alpha-1-antitrypsin or a variant thereof.

DESCRIPTION OF THE FIGURES

FIGS. 1–1C depict the amino acid sequence currently thought to be the most representative of natural HSA, with (boxed) the alternative C-termini of HSA(1–n);

FIGS. 2–2C depict the DNA sequence coding for mature HSA, wherein the sequence included in Linker 3 is underlined;

FIG. 4 illustrates, diagrammatically, the construction of pHOB31;

FIGS. 5–5M illustrate the mature protein sequence encoded by the Fn plasmid pFHDEL1;

FIG. 6 illustrates Linker 5, showing the eight constituent oligonucleotides;

FIG. 7 shows schematically the construction of plasmid pDBDF2;

FIG. 8 shows schematically the construction of plasmid pDBDF5;

FIG. 9 shows schematically the construction of plasmid pDBDF9;

FIG. 11 shows a map of plasmid pFHDEL1;

FIGS. 12–12B show the DNA sequence of human mature urokinase-type plasminogen activator (uPA) and indicates the positions at which the PCR primers used in Example 5 anneal; and FIG. 13 shows schematically the construction of plasmid pDBPF14.

DETAILED DESCRIPTION OF PREFERRED EMBODIMENTS

Figure 3:
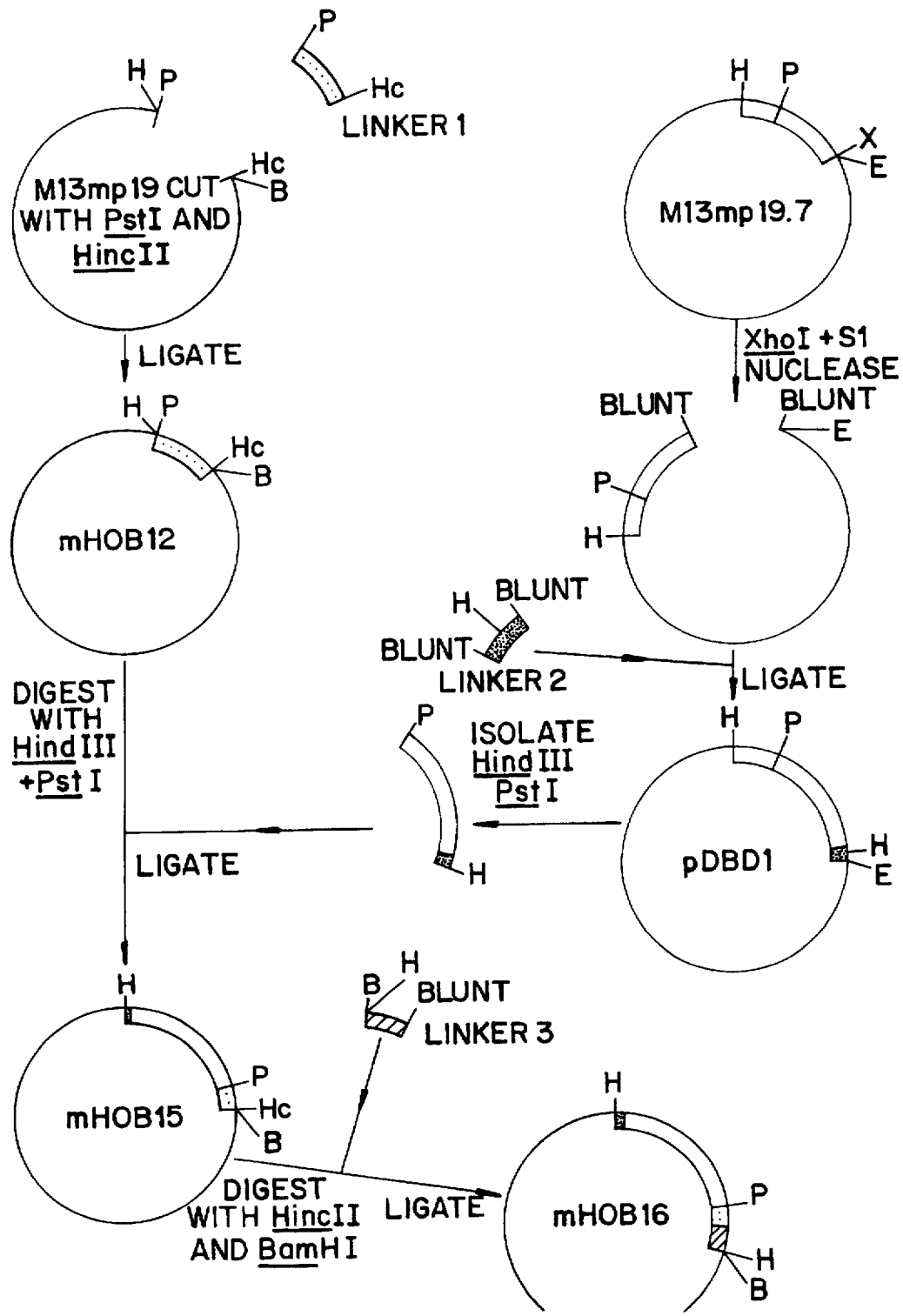
FIG. 3 illustrates, diagrammatically, the construction of mHOB16.

By "N-terminal portion of HSA", we mean any N-terminal portion, ie any compound which includes the native N-terminal region of 10 amino acids but which does not include the C-terminal amino acid. Preferably, the said portion is the 1–450 region or less. The N-terminal portion of HSA is more preferably the said 1–n portion, the 1–177 portion (up to and including the cysteine), the 1–199 portion (up to but excluding the cysteine) or a portion intermediate 1–177 and 1–199. HSA (1–194) is an example of the latter.

The term "human serum albumin" (HSA) is intended to include (but not necessarily to be restricted to) known or yet-to-be-discovered polymorphic forms of HSA. For example, albumin Naskapi has Lys-372 in place of Glu-372 and pro-albumin Christchurch has an altered pro-sequence. The term "variants" is intended to include (but not necessarily to be restricted to) minor artificial variations in sequence (such as molecules lacking one or a few residues, having conservative substitutions or minor insertions of residues, or having minor variations of amino acid structure). Thus polypeptides which have 80%, preferably 85%, 90%, 95% or 99%, homology with HSA are deemed to be "variants". It is also preferred for such variants to be physiologically equivalent to HSA; that is to say, variants preferably share at least one pharmacological utility with HSA (for example binding fatty acid or bilirubin or increasing the oncotic potential of the blood). Furthermore, any putative variant which is to be used pharmacologically should be non-immunogenic in the animal (especially human) being treated.

Conservative substitutions are those where one or more amino acids are substituted for others having similar properties such that one skilled in the art of polypeptide chemistry would expect at least the secondary structure, and preferably the tertiary structure, of the polypeptide to be substantially unchanged. For example, typical such substitutions include asparagine for glutamine, serine for threonine or asparagine and arginine for lysine. Variants may alternatively, or as well, lack up to ten (preferably only one or two) intermediate amino acid residues (ie not at the termini of the said N-terminal portion of HSA) in comparison with the corresponding portion of natural HSA; preferably any such omissions occur in the 100 to 369 portion of the molecule (relative to mature HSA itself) (if present).

Similarly, up to ten, but preferably only one or two, amino acids may be added, again in the 100 to 369 portion for preference (if present). The term "physiologically functional equivalents" also encompasses larger molecules comprising the said sequence plus a further sequence at the N-terminal (for example, pro-HSA, pre-pro-HSA and met-HSA).

Clearly, if the fusion protein consists of the said N-terminal portion of HSA and the said second polypeptide, then the said second polypeptide cannot be the remaining portion of HSA, since otherwise the whole polypeptide would be HSA, which would not then be a "fusion polypeptide".

Even when the HSA-like portion is not the said 1–n portion of HSA, it is preferred for said second polypeptide to be one of the said (a) to (h) entities or the amino terminal fragment (1–134) of human urokinase-type plasminogen activator (uPA).

The 1 to 368 portion of CD4 represents the first four disulphide-linked immunoglobulin-like domains of the human T lymphocyte CD4 protein, the gene for and amino acid sequence of which are disclosed in D. Smith et al (1987) *Science* 328, 1704–1707. It is used to combat HIV infections.

The sequence of human platelet-derived growth factor (PDGF) is described in Collins et al (1985) *Nature* 316, 748–750. Similarly, the sequence of transforming growth factors β (TGF-β) is described in Derynck et al (1985) *Nature* 316, 701–705. These growth factors are useful for wound-healing.

A cDNA sequence for the 1–261 portion of Fn was disclosed in EP-A-207 751 (obtained from plasmid pFH6 with endonuclease PvuII). This portion binds fibrin and can be used to direct fused compounds to blood clots.

A cDNA sequence for the 278–578 portion of Fn, which contains a collagen-binding domain, was disclosed by R. J. Owens and F. E. Baralle in 1986 *E.M.B.O.J.* 5, 2825–2830. This portion will bind to platelets.

The 1–272 portion of von Willebrand's Factor binds and stabilises factor VIII. The sequence is given in Bontham et al, *Nucl. Acids Res.* 14, 7125–7127.

Variants of alpha-1-antitrypsin include those disclosed by Rosenburg et al (1984) *Nature* 312, 77–80. In particular, the present invention includes the Pittsburgh variant (Met$^{358}$ is mutated to Arg) and the variant where Pro$^{357}$ and Met$^{358}$ are mutated to alanine and arginine respectively. These compounds are useful in the treatment of septic shock and lung disorders.

Urokinase type plasminogen activator (uPA) consists of three distinct domains, a growth factor or EGF domain, a kringle domain and a protease domain. Upon activation of the zymogen single chain molecule by cleavage at K158-I159 a two chain molecule linked by a disulphide bond is formed. Further autocatalytic cleavage liberates the so-called amino terminal fragment (ATF), consisting of the growth factor and kringle domains (amino acids 1–135) from the remainder of the molecule. This amino terminal portion of the molecule retains the ability to bind to a specific cell surface receptor for uPA (uPAR).

HSA (1–194) can be used to facilitate the secretion of ATF in *S. cerevisiae* and, surprisingly, we have found that by placing a linker peptide which includes a site for cleavage by the protease specified by the *S. cerevisiae* KEX2 gene, namely protease yscF, the two moieties are cleaved in vivo and are both secreted into the medium. The KEX2-encoded protease cleaves C-terminal to pairs of basic residues, ie Lys-Arg, Arg-Arg or, less readily, Lys-Lys. The HSA primary sequence contains four potential KEX2-encoded protease cleavage sites (R144,R145; K159, R160; R336, R337; R484, R485) and four less favoured sites (K136, K137; K413, K414; K524, K525; K573, K574) yet none of these appears to be recognised by the protease (Sleep et al, 1990). However, positioning of the sequence SLDKR C-terminal to HSA 1–194 and followed by uPA 1–134 leads to KEX2-dependent cleavage of the molecule whereas the R144R145, K159R160 and K136K137 potential KEX2 sites in the HSA moiety and K35K36 of ATF are not recognised by the protease to any detectable degree.

The sequence of urokinase-type plasminogen activator (uPA) is given in FIG. 12. The amino terminal fragment thereof (1–134) is useful in targeting compounds to the uPA receptor, which is found in increased numbers on tumours.

Variants of the second polypeptide include variations as discussed above in relation to the HSA portion, including those with conservative amino acid substitutions, and also homologues from other species.

The fusion polypeptides of the invention may have N-terminal amino acids which extend beyond (in an N-terminal direction) the portion corresponding to the N-terminal portion of HSA. For example, if the HSA-like portion corresponds to an N-terminal portion of mature HSA, then pre-, pro-, or pre-pro sequences may be added thereto, for example the yeast alpha-factor leader sequence. The fused leader portions of WO 90/01063 may be used. The polypeptide which is fused to the HSA portion may be a naturally-occurring polypeptide, a fragment thereof or a novel polypeptide, including a fusion polypeptide. For example, in Example 3 below, a fragment of fibronectin is fused to the HSA portion via a 4 amino acid linker. The molecules of the invention, when comprising a second polypeptide selected from (a)–(h) above, may have further amino acids to provide a C-terminal end but it is preferred for the (a)–(h) entity to constitute the C-terminal end. Similarly, it is within the scope of the invention to include further amino acids between the HSA-derived portion and the (a)–(h) entity. The insertion of a KEX2 cleavage site as described above is a specific example of this.

It has been found that the amino terminal portion of the HSA molecule is so structured as to favour particularly efficient translocation and export of the fusion compounds of the invention in eukaryotic cells.

A second aspect of the invention provides a transformed host having a nucleotide sequence so arranged as to express a fusion polypeptide as described above. By "so arranged", we mean, for example, that the nucleotide sequence is downstream from an appropriate RNA polymerase binding site, is in correct reading frame with a translation start sequence and is under the control of a suitable promoter. The promoter may be homologous with or heterologous to the host. Downstream (3') regulatory sequences may be included if desired, as is known. The host is preferably yeast (for example Saccharomyces spp., e.g. *S. cerevisiae;* Kluyveromyces spp., e.g. *K. lactis;* Pichia spp.; or Schizosaccharomyces spp., e.g. *S. pombe*) but may be any other suitable host such as *E. coli, B. subtilis,* Aspergillus spp., mammalian cells, plant cells or insect cells.

Yeast cells can be transformed by: (a) digestion of the cell walls to produce spheroplasts; (b) mixing the spheroplasts with transforming DNA (derived from a variety of sources and containing both native and non-native DNA sequences); and (c) regenerating the transformed cells. The regenerated cells are then screened for the incorporation of the transforming DNA.

It has been demonstrated that yeast cells of the genera Pichia, Saccharomyces, Kluyveromyces, Yarrowia and Hansenula can be transformed by enzymatic digestion of the cell walls to give spheroplasts; the spheroplasts are then mixed with the transforming DNA and incubated in the presence of calcium ions and polyethylene glycol, then transformed spheroplasts are regenerated in regeneration medium.

Methods for the transformation of *S. cerevisiae* are taught generally in U.S. Pat. No. 4,937,193, which is incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, and hybrid promoters involving hybrids of parts of 5' regulatory regions with parts of 5' regulatory regions of other promoters or with upstream activation sites (eg the promoter of EPA-258067). The preferred promoter is the PRB1 promoter.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, ie may correspond to the promoter. Alternatively, they may be different in which case the termination signal of the *S. cerevisiae* ADH1 gene is preferred.

Suitable secretion leader sequences, if the molecule is to be secreted from the host, include mammalian leader sequences, such as the HSA and pro-uPA leader sequences, *S. cerevisiae* leader sequences such as the α-mating factor pheromone pre- and prepro- sequence, the invertase (SUC2) leader sequence, the PHO5 leader sequence, or hybrid leader sequences such as the leader sequence of WO 90/01063 (U.S. Ser. No. 460,165).

A third aspect of the invention provides a process for preparing a fusion polypeptide according to the first aspect of the invention by cultivation of a transformed host according to the second aspect of the invention, followed by separation of the fusion polypeptide or the non-HSA portion thereof in a useful form.

A fourth aspect of the invention provides therapeutic methods of treatment of the human or other animal body comprising administration of such a fusion polypeptide.

In the methods of the invention we are particularly concerned to improve the efficiency of secretion of useful therapeutic human proteins from yeast and have conceived the idea of fusing to amino-terminal portions of HSA those proteins which may ordinarily be only inefficiently secreted. One such protein is a potentially valuable wound-healing polypeptide representing amino acids 585 to 1578 of human fibronectin (referred to herein as Fn 585–1578). This molecule contains cell spreading, chemotactic and chemokinetic activities useful in healing wounds. The fusion polypeptides of the present invention wherein the C-terminal portion is Fn 585–1578 can be used for wound healing applications as biosynthesised, especially where the hybrid human protein will be topically applied. However, the portion representing amino acids 585 to 1578 of human fibronectin can if desired be recovered from the fusion protein by preceding the first amino acid of the fibronectin portion by amino acids comprising a factor X cleavage site. After isolation of the fusion protein from culture supernatant, the desired molecule is released by factor X cleavage and purified by suitable chromatography (eg ion-exchange chromatography). Other sites providing for enzymatic or chemical cleavage can be provided, either by appropriate juxtaposition of the N-terminal and C-terminal portions or by the insertion therebetween of an appropriate linker.

At least some of the fusion polypeptides of the invention, especially those including the said CD4 and vWF fragments, PDGF and $\alpha_1$AT, also have an increased half-life in the blood and therefore have advantages and therapeutic utilities themselves, namely the therapeutic utility of the non-HSA portion of the molecule. In the case of $\alpha_1$AT and others, the compound will normally be administered as a one-off dose or only a few doses over a short period, rather than over a long period, and therefore the compounds are less likely to cause an immune response.

EXAMPLES

SUMMARY

Standard recombinant DNA procedures were as described by Maniatis et al (1982) and the 2nd edition thereof (Sambrook et al 1989) unless otherwise stated. Construction and analysis of phage M13 recombinant clones was as described by Messing (1983) and Sanger et al (1977).

DNA sequences encoding portions of human serum albumin used in the construction of the following molecules are derived from the plasmids mHOB12 and pDBD2 (EP-A-322 094, U.S. Ser. No. 687,211, Delta Biotechnology Ltd, relevant portions of which are reproduced below) or by synthesis of oligonucleotides equivalent to parts of this sequence. DNA sequences encoding portions of human fibronectin are derived from the plasmid pFHDEL1, or by synthesis of oligonucleotides equivalent to parts of this sequence. Plasmid pFHDEL1, which contains the complete human cDNA encoding plasma fibronectin, was obtained by ligation of DNA derived from plasmids pFH6, 16, 54, 154 and 1 (EP-A-207 751; Delta Biotechnology Ltd).

This DNA represents an mRNA variant which does not contain the 'ED' sequence and had an 89-amino acid variant of the III-CS region (R. J. Owens, A. R. Kornblihtt and F. E. Baralle (1986) *Oxford Surveys on Eukaryotic Genes* 3, 141–160). The map of this vector is disclosed in FIG. 11 and the protein sequence of the mature polypeptide produced by expression of this cDNA is shown in FIG. 5.

Oligonucleotides were synthesised on an Applied Biosystems 380B oligonucleotide synthesiser according to the manufacturer's recommendations (Applied Biosystems, Warrington, Cheshire, UK).

An expression vector was constructed in which DNA encoding the HSA secretion signal and mature HSA up to and including the 387th amino acid, leucine, fused in frame to DNA encoding a segment of human fibronectin representing amino acids 585 to 1578 inclusive, was placed downstream of the hybrid promoter of EP-A-258 067 (U.S. Ser. No. 577,815, Delta Biotechnology), which is a highly efficient galactose-inducible promoter functional in *Saccharomyces cerevisiae*. The codon for the 1578th amino acid of human fibronectin was directly followed by a stop codon (TAA) and then the *S. cerevisiae* phosphoglycerate kinase (PGK) gene transcription terminator. This vector was then introduced into *S. cerevisiae* by transformation, wherein it directed the expression and secretion from the cells of a hybrid molecule representing the N-terminal 387 amino acids of HSA C-terminally fused to amino acids 585 to 1578 of human fibronectin.

In a second example a similar vector is constructed so as to enable secretion by *S. cerevisiae* of a hybrid molecule representing the N-terminal 195 amino acids of HSA C-terminally fused to amino acids 585 to 1578 of human fibronectin.

Example 1

HSA 1–387 Fused to Fn 585–1578

The following is an account of a preparation of plasmids comprising sequences encoding a portion of HSA, as is disclosed in EP-A-322 094.

The human serum albumin coding sequence used in the construction of the following molecules is derived from the plasmid M13mp19.7 (EP-A-201 239, U.S. Ser. No. 854,751, Delta Biotechnology Ltd) or by synthesis of oligonucleotides equivalent to parts of this sequence. Oligonucleotides were synthesised using phosphoramidite chemistry on an Applied Biosystems 380B oligonucleotide synthesizer according to the manufacturer's recommendations (AB Inc., Warrington, Cheshire, England).

An oligonucleotide was synthesised (Linker 1) which represented a part of the known HSA coding sequence (FIG. 2) from the PstI site (1235–1240, FIG. 2) to the codon for valine 381 qwherein that codon was changed from GTG to GTC:

| | | D | P | H | E | C | Y |
|---|---|---|---|---|---|---|---|
| 5' | | GAT | CCT | CAT | GAA | TGC | TAT |
| 3' | ACGT | CTA | GGA | GTA 1100 | CTT | ACG | ATA |
| | | | | | | | |
| A | K | V | F | D | E | F | K |
| GCC | AAA | GTG | TTC | GAT | GAA | TTT | AAA |
| CGG | TTT | CAC 1120 | AAG | CTA | CTT | AAA | TTT |
| | | | | | | | |
| P | L | V | | | | | |
| CCT | CTT | GTC | 3' | | | | |
| GGA | GGA | CAG | 5' | | | | |

Linker 1 was ligated into the vector M13mp19 (Norrander et al, 1983) which had been digested with PstI and HincII and the ligation mixture was used to transfect *E. coli* strain XL1-Blue (Stratagene Cloning Systems, San Diego, Calif.). Recombinant clones were identified by their failure to evolve a blue colour on medium containing the chromogenic indicator X-gal (5-bromo-4-chloro-3-indolyl-β-D-galactoside) in the present of IPTG (isopropylthio-β-galactoside). DNA sequence analysis of template DNA prepared from bacteriophage particles of recombinant clones identified a molecule with the required DNA sequence, designated mHOB12 (FIG. 3).

M13mp19.7 consists of the coding region of mature HSA in M13mp19 (Norrander et al, 1983) such that the codon for the first amino acid of HSA, GAT, overlaps a unique XhoI site thus:

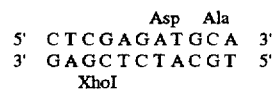

(EP-A-210 239). M13mp19.7 was digested with XhoI and made flush-ended by S1-nuclease treatment and was then ligated with the following oligonucleotide (Linker 2):

The ligation mix was then used to transfect *E. coli* XL1-Blue and template DNA was prepared from several plaques and then analysed by DNA sequencing to identify a clone, pDBD1 (FIG. 3), with the correct sequence.

A 1.1 kb HindIII to PstI fragment representing the 5' end of the HSA coding region and one half of the inserted oligonucleotide linker was isolated from pDBD1 by agarose gel electrophoresis. This fragment was then ligated with double stranded mHOB12 previously digested with HindIII and PstI and the ligation mix was then used to transfect *E. coli* XL1-Blue. Single stranded template DNA was prepared from mature bacteriophage particles of several plaques. The DNA was made double stranded in vitro by extension from annealed sequencing primer with the Klenow fragment of DNA polymerase I in the presence of deoxynucleoside triphosphates. Restriction enzyme analysis of this DNA permitted the identification of a clone with the correct configuration, mHOB15 (FIG. 3).

The following oligonucleotide (Linker 3) represents from the codon for the 382nd amino acid of mature HSA (glutamate, GAA) to the codon for lysine 389 which is followed by a stop codon (TAA) and a HindIII site and then a BamHI cohesive end:

This was ligated into double stranded mHOB15, previously digested with HincII and BamHI. After ligation, the DNA was digested with HincII to destroy all non-recombinant molecules and then used to transfect *E. coli* XL1-Blue. Single stranded DNA was prepared from bacteriophage particles of a number of clones and subjected to DNA sequence analysis. One clone having the correct DNA sequence was designated mHOB16 (FIG. 3).

A molecule in which the mature HSA coding region was fused to the HSA secretion signal was created by insertion of Linker 4 into BamHI and XhoI digested M13mp19.7 to form pDBD2 (FIG. 4).

the fibronectin sequence of EP-A-207 751 to the codon for tyrosine 1578 (FIG. 5) which is followed by a stop codon (TAA), a HindIII site and then a BamHI cohesive end:

| Linker 6 | | | | | | | | | | | | |
|---|---|---|---|---|---|---|---|---|---|---|---|---|
| | | G | P | D | Q | T | E | M | T | I | E | G | L |
| | | GGT | CCA | GAT | CAA | ACA | GAA | ATG | ACT | ATT | GAA | GGC | TTG |
| A | CGT | CCA | GGT | CTA | GTT | TGT | CTT | TAC | TGA | TAA | CTT | CCG | AAC |
| Q | P | T | V | E | Y | Stop | | | | | | |
| CAG | CCC | ACA | GTG | GAG | TAT | TAA | GCTTG | | | | | |
| GTC | GGG | TGT | CAC | CTC | ATA | ATT | CGAACCTAG | | | | | |

| Linker 4 | | | | | | |
|---|---|---|---|---|---|---|
| | | M | K | W | V | S | F |
| 5' | GATCC | ATG | AAG | TGG | GTA | AGC | TTT |
| | G | TAC | TTC | ACC | CAT | TCG | AAA |
| I | S | L | L | F | L | F | S |
| ATT | TCC | CTT | CTT | TTT | CTC | TTT | AGC |
| TAA | AGG | GAA | GAA | AAA | GAG | AAA | TCG |
| S | A | Y | S | R | G | V | F |
| TCG | GCT | TAT | TCC | AGG | GGT | GTG | TTT |
| AGC | CGA | ATA | AGG | TCC | CCA | CAC | AAA |
| R | R | | | | | | |
| CG | 3' | | | | | | |
| GCAGCT | 5' | | | | | | |

In this linker the codon for the fourth amino acid after the initial methionine, ACC for threonine in the HSA pre-pro leader sequence (Lawn et al, 1981), has been changed to AGC for serine to create a HindIII site.

A sequence of synthetic DNA representing a part of the known HSA coding sequence (Lawn et al, 1981) (amino acids 382 to 387, FIG. 2), fused to part of the known fibronectin coding sequence (Kornblihtt et al, 1985) (amino acids 585 to 640, FIG. 2), was prepared by synthesising six oligonucleotides (Linker 5, FIG. 6). The oligonucleotides 2, 3, 4, 6, 7 and 8 were phosphorylated using T4 polynucleotide kinase and then the oligonucleotides were annealed under standard conditions in pairs, ie 1+8, 2+7, 3+6 and 4+5. The annealed oligonucleotides were then mixed together and ligated with mHOB12 which had previously been digested with the restriction enzymes HincII and ECoRI. The ligation mixture was then used to transfect E. coli XL1-Blue (Stratagene Cloning Systems, San Diego, Calif.). Single stranded template DNA was then prepared from mature bacteriophage particles derived from several independent plaques and then was analysed by DNA sequencing. A clone in which a linker of the expected sequence had been correctly inserted into the vector was designated pDBDF1 (FIG. 7). This plasmid was then digested with PstI and ECoRI and the approx. 0.24 kb fragment was purified and then ligated with the 1.29 kb BamHI-PstI fragment of pDBD2 (FIG. 7) and BamHI+ECoRI digested pUC19 (Yanisch-Perron, et al, 1985) to form pDBDF2 (FIG. 7).

A plasmid containing a DNA sequence encoding full length human fibronectin, pFHDEL1, was digested with EcoRI and XhoI and a 0.77 kb EcoRI-XhoI fragment (FIG. 8) was isolated and then ligated with EcoRI and SalI digested M13 mp18 (Norrander et al, 1983) to form pDBDF3 (FIG. 8).

The following oligonucleotide linker (Linker 6) was synthesised, representing from the PstI site at 4784–4791 of This linker was then ligated with PstI and HindIII digested pDBDF3 to form pDBDF4 (FIG. 8). The following DNA fragments were then ligated together with BglII digested pKV50 (EP-A-258 067) as shown in FIG. 8: 0.68 kb EcoRI-BamHI fragment of pDBDF4, 1.5 kb BamHI-StuI fragment of pDBDF2 and the 2.2 kb StuI-EcoRI fragment of pFHDEL1. The resultant plasmid pDBDF5 (FIG. 8) includes the promoter of EP-A-258 067 to direct the expression of the HSA secretion signal fused to DNA encoding amino acids 1–387 of mature HSA, in turn fused directly and in frame with DNA encoding amino acids 585–1578 of human fibronectin, after which translation would terminate at the stop codon TAA. This is then followed by the S. cerevisiae PGK gene transcription terminator. The plasmid also contains sequences which permit selection and maintenance in Escherichia coli and S. cerevisiae (EP-A-258 067).

This plasmid was introduced into S. cerevisiae S150-2B (leu2-3 leu2-112 ura3-52 trp1-289 his3-1) by standard procedures (Beggs, 1978). Transformants were subsequently analysed and found to produce the HSA-fibronectin fusion protein.

Example 2

HSA 1–195 Fused to Fn 585–1578

In this second example the first domain of human serum albumin (amino acids 1–195) is fused to amino acids 585–1578 of human fibronectin.

The plasmid pDBD2 was digested with BamHI and BglII and the 0.79 kb fragment was purified and then ligated with BamHI-digested M13mp19 to form pDBDF6 (FIG. 9). The following oligonucleotide:

5'-CCAAAGCTCGAGGAACTTCG-3' was used as a mutagenic primer to create a XhoI site in pDBDF6 by in vitro mutagenesis using a kit supplied by Amersham International PLC. This site was created by changing base number 696 of HSA from a T to a G (FIG. 2). The plasmid thus formed was designated pDBDF7 (FIG. 9). The following linker was then synthesised to represent from this newly created XhoI site to the codon for lysine 195 of HSA (AAA) and then from the codon for isoleucine 585 of fibronectin to the ends of oligonucleotides 1 and 8 shown in FIG. 6.

| Linker 7 |
|---|

```
     D    E    L    R    D    E    G    K    A    S    S    A    K
TC  GAT  GAA  CTT  CGG  GAT  GAA  GGG  AAG  GCT  TCG  TCT  GCC  AAA
     A   CTT  GAA  GCC  CTA  CTT  CCC  TTC  CGA  AGC  AGA  CGG  TTT

I    T    E    T    P    S    Q    P    N    S    H
    ATC  ACT  GAG  ACT  CCG  AGT  CAG  C
    TAG  TGA  CTC  TGA  GGC  TCA  GTC  GGG  TTG  AGG  GTG  G
```

This linker was ligated with the annealed oligonucleotides shown in FIG. 3, ie 2+7, 3+6 and 4+5 together with XhoI and ECoRI digested pDBDF7 to form pDBDF8 (FIG. 9). Note that in order to recreate the original HSA DNA sequence, and hence amino acid sequence, insertion of linker 7 and the other oligonucleotides into pDBDF7 does not recreate the XhoI site.

The 0.83 kb BamHI-StuI fragment of pDBDF8 was purified and then was ligated with the 0.68 kb EcoRI-BamHI fragment of pDBDF4 and the 2.22 kb StuI-EcoRI fragment of pFHDEL1 into BglII-digested pKV50 to form pDBDF9 (FIG. 9). This plasmid is similar to pDBDF5 except that it specifies only residues 1–195 of HSA rather than 1–387 as in pDBDF5.

When introduced into *S. cerevisiae* S150-2B as above, the plasmid directed the expression and secretion of a hybrid molecule composed of residues 1–195 of HSA fused to residues 585–1578 of fibronectin.

Example 3

HSA 1–387 Fused to Fn 585–1578, as Cleavable Molecule

In order to facilitate production of large amounts of residues 585–1578 of fibronectin, a construct was made in which DNA encoding residues 1–387 of HSA was separated from DNA encoding residues 585–1578 of fibronectin by the sequence

```
     I    E    G    R
    ATT  GAA  GGT  AGA
    TAA  CTT  CCA  TCT
``` which specifies the cleavage recognition site for the blood clotting Factor X. Consequently the purified secreted product can be treated with Factor X and then the fibronectin part of the molecule can be separated from the HSA part.

To do this two oligonucleotides were synthesised and then annealed to form Linker 8.

| Linker 8 |
|---|

```
    E    E    P    Q    N    L    I    E    G
   GAA  GAG  CCT  CAG  AAT  TTA  ATT  GAA  GGT
   CTT  CTC  GGA  GTC  TTA  AAT  TAA  CTT  CCA

R    I    T    E    T    P    S    Q    P
   AGA  ATC  ACT  GAG  ACT  CCG  AGT  CAG  C
   TCT  TAG  TGA  CTC  TGA  GGC  TCA  GTC  GGG

N    S    H
   TTG  AGG  GTG  G
```

Figure 10:
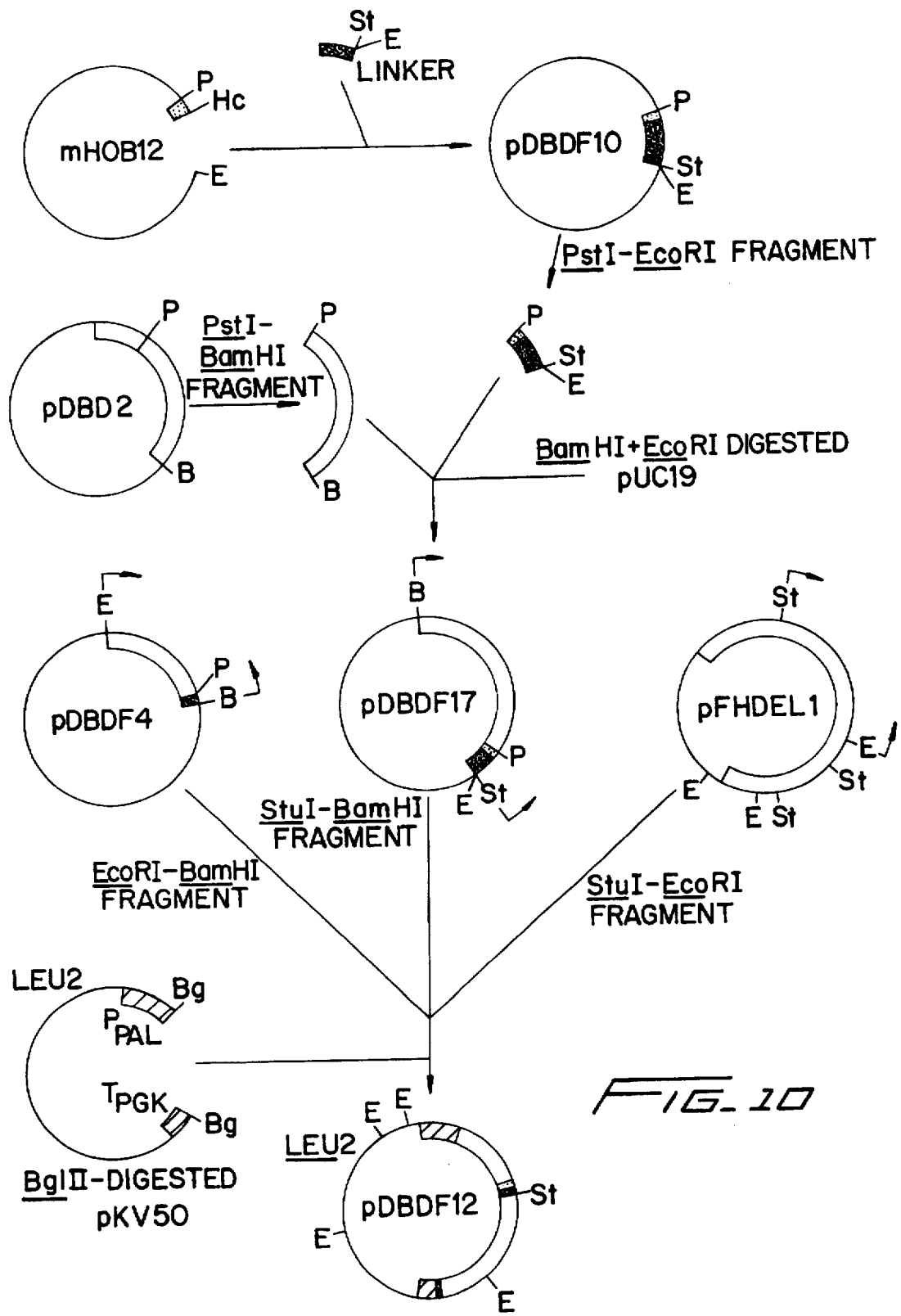
FIG. 10 shows schematically the construction of plasmid DBDF12, using plasmid pFHDEL1.

This linker was then ligated with the annealed oligonucleotides shown in FIG. 6, ie 2+7, 3+6 and 4+5 into HincII and EcoRI digested mHOB12, to form pDBDF10 (FIG. 10). The plasmid was then digested with PstI and ECoRI and the roughly 0.24 kb fragment was purified and then ligated with the 1.29 kb BamHI-PstI fragment of pDBD2 and BamHI and EcoRI digested pUC19 to form pDBDF17 (FIG. 10).

The 1.5 kb BamHI-StuI fragment of pDBDF11 was then ligated with the 0.68 kb EcoRI-BamHI fragment of pDBDF4 and the 2.22 kb StuI-EcoRI fragment of pFHDEL1 into BglII-digested pKV50 to form pDBDF12 (FIG. 10). This plasmid was then introduced into *S. cerevisiae* S150-2B. The purified secreted fusion protein was treated with Factor X to liberate the fibronectin fragment representing residues 585–1578 of the native molecule.

Example 4

HSA 1–194 Fused to Urokinase 1–134, as a Molecule Cleavable In Vivo

The following oligonucleotide linker (linker 9) encoding amino acids 183–194 of HSA followed by the amino acid sequence SLDKR and amino acids 1–7 of uPA was ligated with XhoI+KpnI-digested pDBDF7 to form pDBDF13 (FIG. 13).

Linker 9

```
                              HSA
        D    E    L    R    D    E    G    K    A    S    S    A  | S    L
    TCGAT   GAA  CTT  CGG  GAT  GAA  GGG  AAG  GCT  TCG  TCT  GCC   AGC  TTG
       A   CTT  GAA  GCC  CTA  CTT  CCC  TTC  CGA  CGC  AGA  CGG   TCG  AAC
```

```
         KEX2 spacer            -continued
                                  uPA
         ┌─────────┐  ┌─────────────────────────┐
          D   K   R    S   N   E   L   H   Q   V
         GAT AAA AGA  AGC AAT GAA CTT CAT CAG GTA C
         CTA TTT TCT  TCG TTA CTT GAA GTA GTC
```

DNA encoding the amino terminal fragment of uPA was obtained using polymerase chain reaction (PCR, Saiki et al, 1985) amplification of DNA prepared from a cDNA library. Bacteriophage lambda DNA was prepared from a U937 cDNA library (Clontech Laboratories, Inc., Palo Alto, USA, Catalogue No. HL1036b) plated on *E. coli* Y1090 (Clontech Cat. No. C1092-1) by the plate lysate method (Maniatis et al, 1982). Two oligonucleotides were synthesised for amplification of the ATF coding sequence and represented the two extremes of the sequence required (see FIG. 12).

Oligonucleotide 9

5'-GCTACGGTACCATCGAACTGTGACTGTTCTAAATGG-3'
         └────┘
          KpnI

Oligonucleotide 10

5'-GCGATCGGATCCTTATCCATCTGCGCAATGGTCCACCATGCA-3'

Oligonucleotide 9 corresponds to the sequence encoding amino acids 7-13 and includes a KpnI site not normally present in the uPA cDNA but does not alter the encoded amino acid sequence. Oligonucleotide 10 would anneal to the region encoding residues 126-134 of uPA and effectively position a stop codon and a BamHI site 3' to the codon for amino acid 134. PCR was carried out with DNA isolated from the U937 cDNA library and oligos 9 and 10 as primers using a Perkin Elmer-Cetus Gene Amp DNA Amplification Reagent kit and a Perkin Elmer-Cetus DNA thermal cycler in accordance with the manufacturer's recommendations. The PCR product was purified following agarose gel electrophoresis and digested with KpnI and BamHI.

The plasmid pDBDF13 was digested with BamHI and KpnI and the approximately 0.63 kb fragment was purified following agarose gel electrophoresis. This fragment was ligated together with the PCR product into pKV50 to form pDBDF14 (FIG. 13).

This plasmid was then introduced into *S. cerevisiae* S150-2B by transformation. Transformants were subsequently analysed and found to secrete both HSA 1-194+ SLDKR and ATF into the growth medium and no detectable uncleaved fusion protein.

REFERENCES

Beggs, J. D. (1978) *Nature* 275, 104-109
Beggs, J. D. (1981) *Molecular Genetics in Yeast*, Alfred Benzon Symposium 16, 383-395
Contreras et al (1991) *Bio/Technology* 9, 378-381
Kornblihtt et al (1985) *EMBO J.* 4, 1755-1759
Lawn, R. M. et al (1981) *Nucl. Acid. Res.* 9, 6103-6114
Maniatis, T. et al (1982) *Molecular cloning: A laboratory manual*. Cold Spring Harbor Laboratory, Cold Spring Harbor, N.Y.
Messing, J. (1983) *Methods Enzymol.* 101, 20-78
Norrander, J. et al (1983) *Gene* 26, 101-106
Saiki et al (1985) *Science* 230, 1350-1354
Sambrook, J. et al (1989) *Molecular cloning: a laboratory manual*, 2nd edition. Cold Spring Harbor Laboratory Press, Cold Spring Harbor, N.Y.
Sanger, F. et al (1977) *Proc. Natl. Acad. Sci. USA* 74, 5463-5467
Yanisch-Perron, C. (1985) *Gene* 33, 103-119

What we claim is:

1. A fusion polypeptide comprising:

an N-terminal secretion signal providing for secretion into the surrounding medium of said polypeptide from eukaryotic cells in which said polypeptide is expressed, followed by an N-terminal polypeptide portion of HSA or a variant thereof, said variant having at least 80% sequence identify with a length of the N-terminal region of HSA of the same length as said polypeptide, said portion or variant enhancing secretion of said polypeptide; and, as at least part of the C-terminal portion of the fusion polypeptide, a second polypeptide, wherein, when the said N-terminal portion of HSA is the 1–n portion wherein n is 369 to 419 or a variant thereof, said second polypeptide is selected from the group consisting of: (a) the 585 to 1578 portion of human fibronectin or a variant thereof; (b) the 1 to 368 portion of CD4 or a variant thereof; (c) platelet derived growth factor or a variant thereof; (d) transforming growth factor or a variant thereof; (e) the 1–261 portion of mature human plasma fibronectin or a variant thereof; (f) the 278–578 portion of mature human plasma fibronectin or a variant thereof; (g) the 1–272 portion of mature human von Willebrand's Factor or a variant thereof; and (h) alpha-1-antitrypsin or a variant thereof.

2. A fusion polypeptide according to claim 1 wherein there is a cleavable region at the junction of the said N-terminal and C-terminal portions.

3. A fusion polypeptide according to claim 2 wherein said cleavable region is cleavable by the protease encoded by the S. cerevisiae KEX2 gene.

4. A fusion polypeptide according to claim 3 wherein the said C-terminal portion comprises the 1–134/5 amino terminal portion of human urokinase-type plasminogen activator.

5. A fusion polypeptide according to claim 3 wherein the N-terminal portion of HSA is the 1–194 portion.

6. A fusion polypeptide according to claim 4 wherein the N-terminal portion of HSA is the 1–193 portion.

7. A transformed or transfected host eukaryotic cell having a nucleotide sequence encoding a fusion polypeptide according to claim 1 and regulatory regions to allow expression of said nucleotide sequence in said host.

8. A process for preparing a fusion polypeptide comprising:

(1) providing a host eukaryotic cell having a nucleotide sequence encoding a fusion polypeptide, said sequence comprising DNA encoding:

an N-terminal secretion signal providing for secretion of said polypeptide from eukaryotic cells in which said polypeptide is expressed, followed by an N-terminal polypeptide portion of HSA or a variant thereof, said variant having at least 80% sequence identify with a length of the N-terminal region of HSA of the same length as said polypeptide, said portion or variant enhancing secretion of said polypeptide; and, as at least part of the C-terminal portion of the fusion polypeptide, a second polypeptide, wherein when the said N-terminal portion of HSA is the 1–n portion wherein n is 369 to 419 or a variant thereof, said second polypeptide is selected from the group consisting of: (a) the 585 to 1578 portion of human fibronectin or a variant thereof; (b) the 1 to 368 portion of CD4 or a variant thereof; (c) platelet derived growth factor or a variant thereof; (d) transforming growth factor or a variant thereof; (e) the 1–261 portion of mature human plasma fibronectin or a variant thereof; (f) the 278–578 portion of mature human plasma fibronectin or a variant thereof; (g) the 1–272 portion of mature human von Willebrand's Factor or a variant thereof; and (h) alpha-1-antitrypsin or a variant thereof (2) cultivating said cell in a medium such that said fusion polypeptide is expressed and secreted into the medium; and (3) recovering said fusion polypeptide from the medium.

9. A process in accordance with claim 8, wherein said fusion polypeptide includes a cleavable region between said C-terminal and N-terminal regions, said process additionally including the steps of cleaving said fusion polypeptide at said cleavable region during or after secretion of the fusion polypeptide, and recovering the said second polypeptide from the medium.

* * * * *